United States Patent
Yamashita et al.

(10) Patent No.: US 10,695,587 B2
(45) Date of Patent: Jun. 30, 2020

(54) PARTICLE BEAM THERAPY SYSTEM HAVING X-RAY DETECTORS ATTACHED TO A PARTICLE BEAM IRRADIATION SYSTEM

(71) Applicant: Hitachi, Ltd., Tokyo (JP)

(72) Inventors: Tsutomu Yamashita, Tokyo (JP); Tatsuya Fujisawa, Tokyo (JP); Takenori Nishimura, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 23 days.

(21) Appl. No.: 16/106,131

(22) Filed: Aug. 21, 2018

(65) Prior Publication Data

US 2018/0353776 A1  Dec. 13, 2018

Related U.S. Application Data

(63) Continuation of application No. 15/196,140, filed on Jun. 29, 2016, now abandoned.

(30) Foreign Application Priority Data

Jun. 30, 2015 (JP) ................... 2015-131407

(51) Int. Cl.
*A61N 5/10* (2006.01)

(52) U.S. Cl.
CPC ......... *A61N 5/1081* (2013.01); *A61N 5/1049* (2013.01); *A61N 2005/1061* (2013.01); *A61N 2005/1087* (2013.01)

(58) Field of Classification Search
None
See application file for complete search history.

(56) References Cited

U.S. PATENT DOCUMENTS

| | | | |
|---|---|---|---|
| 5,039,867 A | 8/1991 | Nishihara et al. | |
| 5,993,373 A | 11/1999 | Nonaka et al. | |
| 6,307,914 B1 * | 10/2001 | Kunieda | A61B 6/12 378/65 |
| 7,102,144 B2 | 9/2006 | Matsuda et al. | |
| 7,122,811 B2 | 10/2006 | Matsuda et al. | |
| 7,193,227 B2 | 3/2007 | Hiramoto et al. | |

(Continued)

FOREIGN PATENT DOCUMENTS

| | | |
|---|---|---|
| JP | 01-209077 A | 8/1989 |
| JP | 11-047287 A | 2/1999 |

(Continued)

*Primary Examiner* — James Choi
(74) *Attorney, Agent, or Firm* — Mattingly & Malur, PC

(57) ABSTRACT

A particle therapy system has an irradiation system attached to a rotary drum of a gantry. A radiation treatment cage disposed in the rotary drum includes a movable floor including a horizontal floor portion. The movable floor includes a number of footboards connected bendably and X-ray transmission plates. The movable floor has a slide member at each end thereof, and the slide member is movably attached to a guide rail that is provided for each of opposite side surfaces of the irradiation system. X-ray sources are disposed outside the rotary drum apart from each other in a circumferential direction of the rotary drum and attached to the outer surface of the rotary drum. The irradiation system includes X-ray detection systems opposite to the X-ray sources.

18 Claims, 15 Drawing Sheets

(56) References Cited

U.S. PATENT DOCUMENTS

| | | |
|---|---|---|
| 7,227,161 B2 | 6/2007 | Matsuda et al. |
| 7,302,033 B2 | 11/2007 | Carrano et al. |
| 7,405,407 B2 | 7/2008 | Hiramoto et al. |
| 7,425,717 B2 | 9/2008 | Matsuda et al. |
| 7,477,722 B2 | 1/2009 | Carrano et al. |
| 7,560,717 B2 | 7/2009 | Matsuda et al. |
| 2004/0111134 A1* | 6/2004 | Muramatsu ............... A61N 5/10 607/88 |
| 2004/0184583 A1* | 9/2004 | Nagamine ................. A61B 6/04 378/209 |
| 2004/0185683 A1 | 9/2004 | Nakamura |
| 2008/0029706 A1* | 2/2008 | Kaiser ....................... A61N 5/10 250/363.02 |
| 2009/0092228 A1 | 4/2009 | Carrano et al. |
| 2011/0101246 A1 | 5/2011 | Yajima et al. |
| 2011/0299657 A1* | 12/2011 | Havelange ........... A61N 5/1081 378/65 |
| 2017/0340903 A1* | 11/2017 | Ie ......................... A61B 6/4452 |
| 2018/0289981 A1* | 10/2018 | Nagamoto ............... A61B 6/12 |

FOREIGN PATENT DOCUMENTS

| | | |
|---|---|---|
| JP | 2004-358237 A | 12/2004 |
| JP | 2006-239403 A | 9/2006 |
| JP | 2008-544833 A | 12/2008 |
| JP | 2011-092424 A | 5/2011 |
| JP | 2011-156263 A | 8/2011 |

\* cited by examiner

PARTICLE BEAM THERAPY SYSTEM HAVING X-RAY DETECTORS ATTACHED TO A PARTICLE BEAM IRRADIATION SYSTEM

BACKGROUND OF THE INVENTION

1. Field of the Invention

The present invention relates to a particle therapy system suitably used for treating cancer with a particle beam, which is one kind of radiation.

2. Description of the Related Art

Particle therapy systems that deliver a particle beam (proton or baryon beam) to a target volume in accordance with its position and shape have been used in, for example, cancer treatment.

Known particle therapy systems are roughly classified into particle therapy systems with a synchrotron as an accelerator (for example, JP-2004-358237-A) and particle therapy systems with a cyclotron as an accelerator (for example, JP-2011-92424-A). The particle therapy system with the synchrotron and the particle therapy system with the cyclotron both have a gantry provided with an irradiation system.

For the particle therapy to be efficiently conducted, it is necessary to deliver the particle beam to the cancer lesion with high accuracy, and in view of this, particle therapy systems with the structure that enables to set the irradiation system to the optimum irradiation point of the patient have been developed. The particle therapy on the patient from any direction with such a particle therapy system requires a gantry system capable of rotating around the patient by 360° and a radiation treatment cage (hereinafter referred to as treatment cage) that operates synchronizing with the rotation.

An example of the gantry with the treatment cage has been disclosed in JP-H-11-47287-A. The treatment cage includes a movable floor, and a rotatable-side ring rail and a fixed-side ring rail disposed inside the gantry and attached to the gantry. The fixed-side ring rail and the rotatable-side ring rail have, on their opposite surfaces, a semi-cylindrical orbit that guides the movable floor. The movable floor includes a number of footboards that are connected with each other in such a manner that the footboards can be freely bent, and the movable floor moves along the semi-cylindrical orbit synchronizing with the rotation of the gantry. Because of the semi-cylindrical orbit, a horizontal floor portion (access floor) is formed by some footboards of the movable floor. The horizontal floor portion enables a medical practitioner (for example, a doctor or a medical technician) to stand on the horizontal floor portion and easily access the patient on the treatment stand inserted into the treatment cage.

An example of the treatment cage installed in the gantry has been disclosed in JP-2011-156263-A. In this treatment cage, the slide members provided at the opposite ends of the movable floor in the circumferential direction of the gantry are slidably attached to a pair of guide rails, which serves as the guide member and is provided for the two side surfaces of the irradiation system attached to the gantry opposite to each other in the rotating direction of the gantry.

JP-2008-544833-T has disclosed in FIG. 10A, FIG. 10B, and FIG. 10C, the radiation therapy system where the image of the patient is formed while the radiation process is carried out. For forming the image, a pair of X-ray sources that emits the X-rays toward a first imaging center and another pair of X-ray sources that emits the X-rays toward a second imaging center are installed within a depression provided for the floor of the operating room and below the floor surface, and the X-ray transparent material is attached to the floor surface covering these X-ray sources.

Moreover, JP-H-1-209077-A has disclosed one example of positioning the target volume relative to the irradiation system. In this positioning method, the amount of movement of the bed for positioning the target volume is calculated using the reference image information formed based on the tomographic information obtained from the X-ray computed tomography system in advance before the position of the target volume and the current X-ray image information in the orthogonal two directions formed based on the X-ray detection signals from the X-ray detection system having detected the X-ray emitted from the X-ray source provided for the irradiation system and transmitted through the target volume of the patient on the bed before the irradiation with the ion beam. Based on the calculated amount of movement of the bed, the bed is moved manually to determine the position of the target volume relative to the irradiation system. According to JP-H-1-209077-A, the bed may be moved automatically based on the calculated amount of movement of the bed.

According to JP-2006-239403-A, the amount of movement of the bed and the rotation angle of the bed are calculated and based on the calculated amount of movement and rotation angle, the target volume is automatically positioned relative to the irradiation system by the bed controller. In JP-2006-239403-A, the target volume is positioned using the reference tomographic information of the target volume obtained from the X-ray computed tomography in advance and the current tomographic image information formed based on the output signals from the X-ray detection system obtained by detecting the X-ray emitted from the X-ray source provided for the irradiation system attached to the gantry and transmitting through the patient on the treatment stand while the gantry is rotated.

SUMMARY OF THE INVENTION

In the particle therapy system including the treatment cage with the movable floor having the positioning driver, the patient on the bed needs to be positioned to the isocenter (bed positioning) after the operation of positioning the treatment cage is completed. In one way of the bed positioning, the X-ray generator and the X-ray detection system (for example, FPD) mounted on the positioning driver provided in the axis direction of the gantry are pulled out to the position of the isocenter and then the patient on the bed is X-rayed.

In the case of using such a positioning driver, however, the operation speed is required to be 100 mm/sec or less from the safety point of view because the operation distance of the X-ray generator is several meters (for example, about 1.8 meters). For this reason, just operating the positioning driver may take ten and several seconds (about 18 seconds). In addition, for the precise positioning, a plurality of such positioning drivers is mounted. If the plural positioning drivers cannot be operated at the same time, the time required for positioning is multiplied by the number of drivers and this is a major issue in improving the treatment throughput.

In one structure to improve the treatment throughput, the movable floor is omitted and a polygonal fixed floor is provided for the treatment cage, and the X-ray generator and the X-ray detection system are fixed at the position where the center axis of the gantry is sectioned at the position of the isocenter. In such a structure, the operation of the positioning driver is not necessary, so that the operation time of the positioning driver is zero, thereby shortening the positioning time. However, the horizontal floor of the treatment cage is formed at a certain pitch in accordance with the number of corners of the polygon and moreover, the treatment cage cannot be increased in size. These facts interrupt the medical practitioner's easy access to the patient.

An object of the present invention is to provide a particle therapy system that enables the medical practitioner to access the patient easily and improves the treatment throughput.

A feature of the present invention for achieving the object is to include: a gantry; an irradiation system which is attached to the gantry and to which an ion beam is incident; a treatment cage installed in the gantry, having an orbit including an arc-like portion and a horizontal portion communicating with the arc-like portion, and including a surrounding member formed by a plurality of connected footboard members and capable of moving along the orbit; an X-ray source disposed outside the surrounding member and attached to the gantry; and an X-ray detection system disposed inside the surrounding member, attached to the irradiation system, and detecting an X-ray from the X-ray source, and the surrounding member includes an X-ray transmission member disposed between the adjacent footboard members, connected to the each of the adjacent footboard members, disposed between the X-ray source and the X-ray detection system, and transmitting an X-ray emitted from the X-ray source.

The surrounding member moving along the orbit including the arc-like portion and the horizontal portion communicating with this arc-like portion forms the horizontal floor portion in the horizontal portion of the orbit. A medical practitioner can stand on the horizontal floor portion and can easily access the patient on the bed inserted into the surrounding member. The X-ray source is attached to the gantry, and the X-ray detection system that detects the X-ray from this X-ray source is attached to the irradiation system. This configuration eliminates the necessity of moving the X-ray source and the X-ray detection system in the axial direction of the gantry in X-raying the target volume. Thus, the time required to start X-raying the target volume can be shortened. This can improve the treatment throughput.

Preferably, the X-ray source is disposed outside the gantry and attached to the outer surface of the gantry and the X-ray transmission hole is formed at the position of the gantry opposite to the X-ray source.

According to the present invention, the medical practitioner can access the patient easily and the treatment throughput can be improved.

BRIEF DESCRIPTION OF THE DRAWINGS

FIG. 3 is 0°;

FIG. 3 is 135°;

FIG. 3 is 180°;

FIG. 3 is 0°;

FIG. 3 is 90°;

FIG. 3 is 180°;

DESCRIPTION OF THE PREFERRED EMBODIMENTS

Embodiments of the present invention will hereinafter be described.

First Embodiment

A particle therapy system according to a first embodiment corresponding to a preferred embodiment of the present invention will hereinafter be described with reference to FIG. 1 to FIG. 4.

Figure 1:
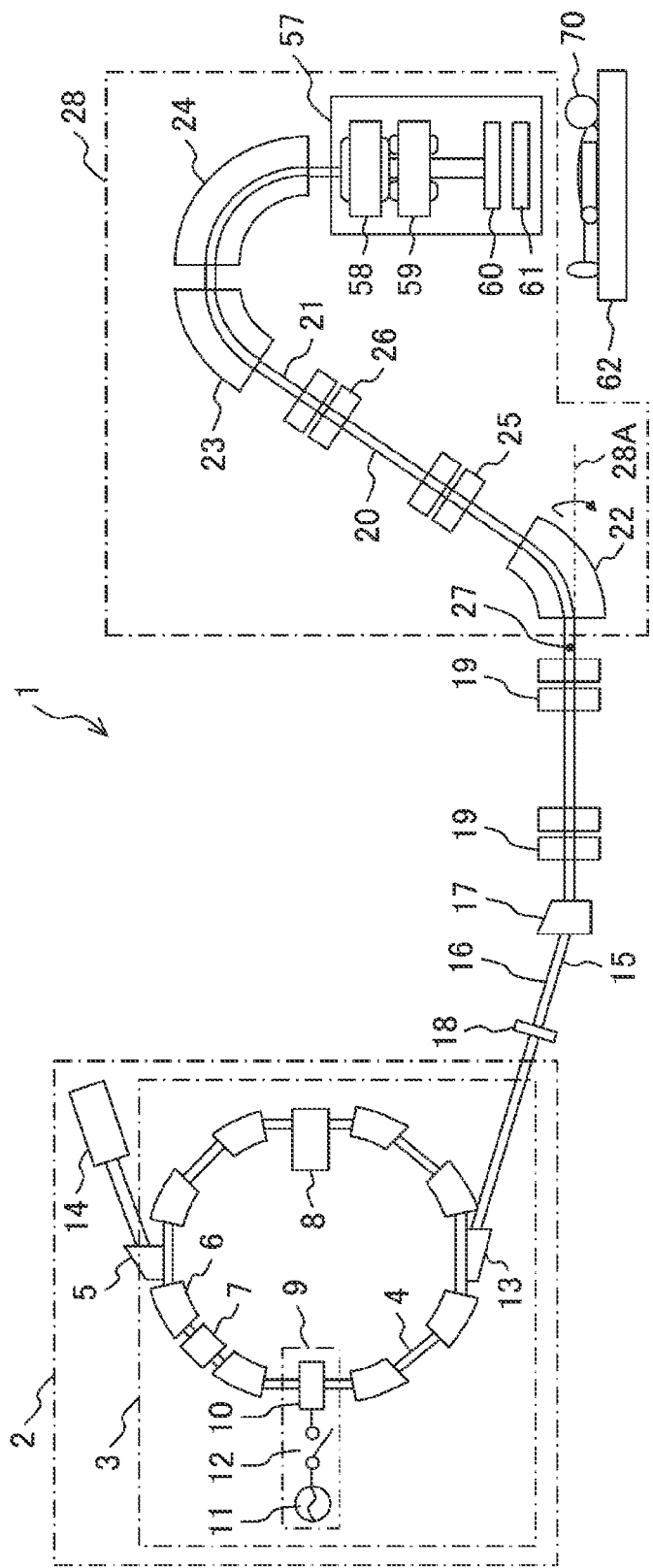
FIG. 1 is a structure diagram illustrating a particle therapy system according to a first embodiment corresponding to a preferred embodiment of the present invention.

A particle therapy system 1 according to this embodiment is installed in a building (not illustrated), specifically on a floor surface of the building. This particle therapy system 1 includes, as illustrated in FIG. 1, an ion beam generator 2, a high energy beam transport (HEBT) 15, a gantry beam transport (GABT) 20, a gantry 28, and an irradiation system 57. The particle therapy system 1 employs a proton ion beam as the ion beam to be delivered to the target volume of the cancer (beam delivery target). A carbon ion beam may be employed instead of the proton ion beam.

The ion beam generator 2 includes an ion source (not illustrated), and a linear accelerator 14 and a synchrotron accelerator 3 corresponding to a preaccelerator. The synchrotron accelerator 3 includes a circular beam duct 4 constituting the circulating orbit of the ion beam, an injector 5, a radiofrequency acceleration cavity (radiofrequency accelerator) 8 that applies radiofrequency voltage to the ion beam, a plurality of bending magnets 6, a plurality of quadrupole magnets 7, an extraction radiofrequency application system 9, and an extraction septum magnet 13. The injector 5 communicating with the beam duct 4 is connected to the linear accelerator 14 through a vacuum duct. The ion source is also connected to the linear accelerator 14. The radiofrequency application system 9 includes an extraction radiofrequency electrode 10, a radiofrequency power source 11, and an opening/closing switch 12. The extraction radiofrequency electrode 10 is attached to the circular beam duct 4, and is connected to the radiofrequency power source 11 through the opening/closing switch 12. The bending magnets 6, the quadrupole magnets 7, the radiofrequency acceleration cavity 8, and the septum magnet 13 are disposed along the beam duct 4 as illustrated in FIG. 1.

The HEBT (first beam transport) 15 includes a beam path (beam duct) 16 connected to the septum magnet 13 of the synchrotron accelerator 3, and is configured to have a plurality of quadrupole magnets 18, a bending magnet 17, and a plurality of quadrupole magnets 19 disposed along the beam path 16 in a direction from the synchrotron accelerator 3 to the irradiation system 57.

The GABT (second beam transport) 20 includes a beam path (beam duct) 21, and is configured to have a bending magnet 22, quadrupole magnets 25 and 26, and bending magnets 23 and 24 disposed along the beam path 21 in a direction from the synchrotron accelerator 3 to the irradiation system 57. The beam path 21 and the magnets of the GABT 20 are attached to the gantry 28. The beam path 21 communicates with the beam path 16 in a scramble portion 27 between the HEBT 15 and the GABT 20. The beam path 21 is rotated by the gantry 28; for this reason, the beam path 21 is not directly connected to the beam path 16.

The irradiation system 57 includes two scanning magnets (ion beam scanning systems) 58 and 59, a beam position monitor 60, and a dose monitor 61. The irradiation system 57 is attached to the gantry 28 in the downstream side relative to the bending magnet 24. The scanning magnets 58 and 59, the beam position monitor 60, and the dose monitor 61 are disposed in this order along a center axis 97 of the irradiation system 57 in a direction from the bending magnet 24 to the ion beam exit of the irradiation system 57. The scanning magnet 58 scans the ion beam in the X direction while having the ion beam bent within a plane perpendicular to the center axis 97 of the irradiation system 57, and the scanning magnet 59 scans the ion beam in the Y direction orthogonal to the X direction while having the ion beam bent within that plane. A treatment stand 62 on which a patient 70 lies down is disposed opposite to the end of the irradiation system 57.

The gantry 28 is described with reference to FIG. 2 and FIG. 3. The gantry 28 includes a semi-cylindrical rotary drum 29 including a front ring 30 and a rear ring 31. The front ring 30 is supported by a support system 32A installed on a floor 72 of the building, and the rear ring 31 is supported by a support system 32B installed on the floor 72. The support system 32A includes a pair of roll supporters 33 and a plurality of support rollers 34A. The support rollers 34A are attached rotatably to each of the roll supporters 33. The front ring 30 is supported by these support rollers 34A.

Like the support system 32A, the support system 32B also includes a pair of roll supporters 33 (not illustrated) and a plurality of support rollers 34B. The support rollers 34B are rotatably attached to each of the roll supporters 33. The rear ring 31 is supported by these support rollers 34B. The gantry 28 is rotated by a rotating system (such as a motor) 49. The rotation system 49 has a rotating shaft thereof connected to the rotating shaft of one of the support rollers 34B that support the rear ring 31 through a decelerator 50. An angle detector 51 that detects the rotating angle of the gantry 28 is connected to the rotating shaft of one of the support rollers 34A that support the front ring 30.

A radiation therapy cage (treatment cage) 35 is installed in the gantry 28. The treatment cage 35 is configured to enable a medical technician 93 (see FIG. 10), for example, to carry out the medical treatment on the patient 70 on the treatment stand 62 while protecting the safety of the patient 70 from the circulating path of the irradiation system 57 in the circumferential direction of the gantry 28. That is to say, it is desirable that the treatment cage 35 provides the scaffolding that enables the medical technician 93 to carry out the medical treatment and besides the scaffolding, provides the closed space from the outside.

The treatment cage 35 includes a movable floor 36, a fixed-side ring rail 45A, a movable-side ring rail 45B, and a back panel 46. The fixed-side ring rail 45A is disposed inside the front ring 30 in accordance with the position of the front ring 30. The movable-side ring rail 45B is disposed opposite to the front ring 30 and on the rear ring 31 side. The irradiation system 57 is disposed between the fixed-side ring rail 45A and the movable-side ring rail 45B. The back panel 46 that accepts the treatment cage 35 in the depth direction is fixed to the movable-side ring rail 45B. The fixed-side ring rail 45A and the movable-side ring rail 45B have their opposite surfaces provided with a semi-cylindrical orbit 76 (see FIG. 7). In this embodiment, the semi-cylindrical shape refers to the shape including the arc-like portion on the upper side and the horizontal portion on the lower side with the opposite ends of the arc-like portion smoothly connecting to the opposite ends of the horizontal portion. The area where the arc-like portion and the horizontal portion are connected refers to the connected portion.

Figure 4:
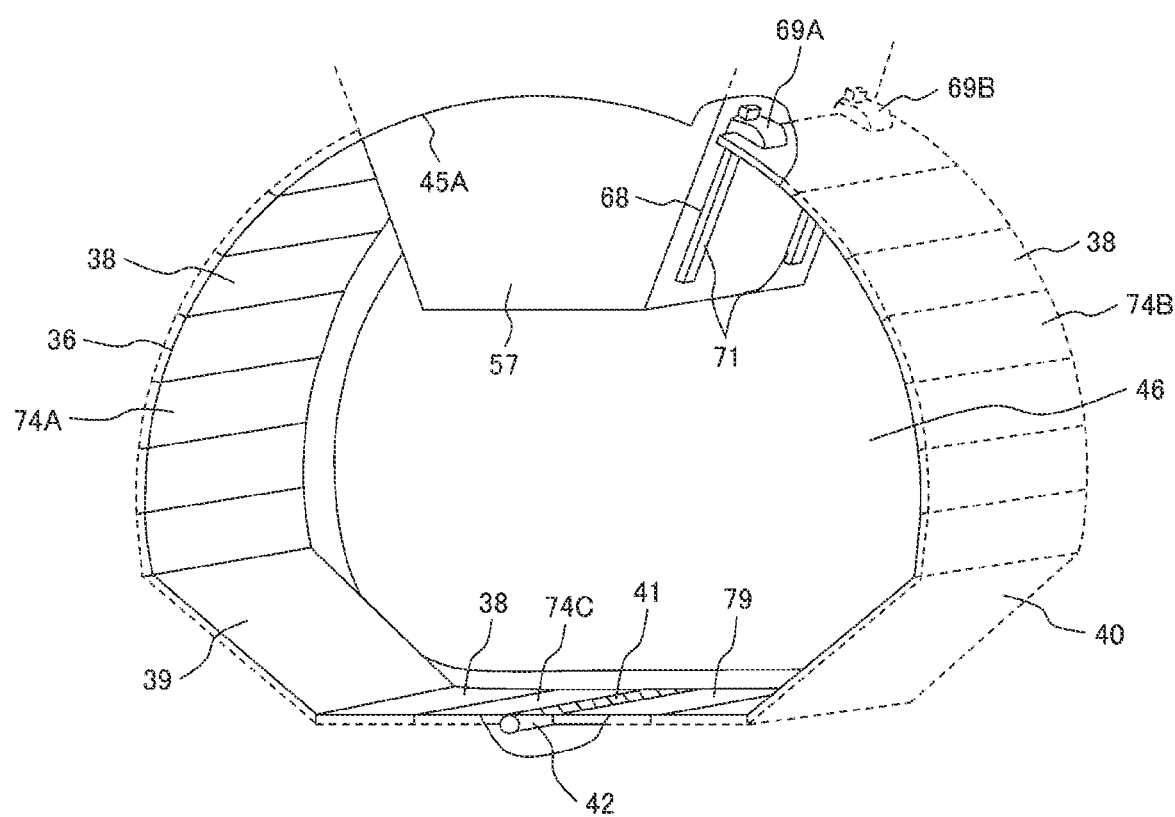
FIG. 4 is a magnified perspective view of a radiation treatment cage illustrated in FIG. 2 and FIG. 3.
Figure 5:
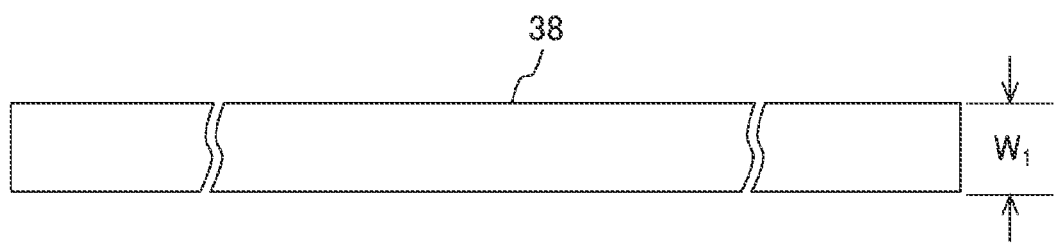
FIG. 5 is a plan view of a footboard illustrated in FIG. 4.
Figure 6:
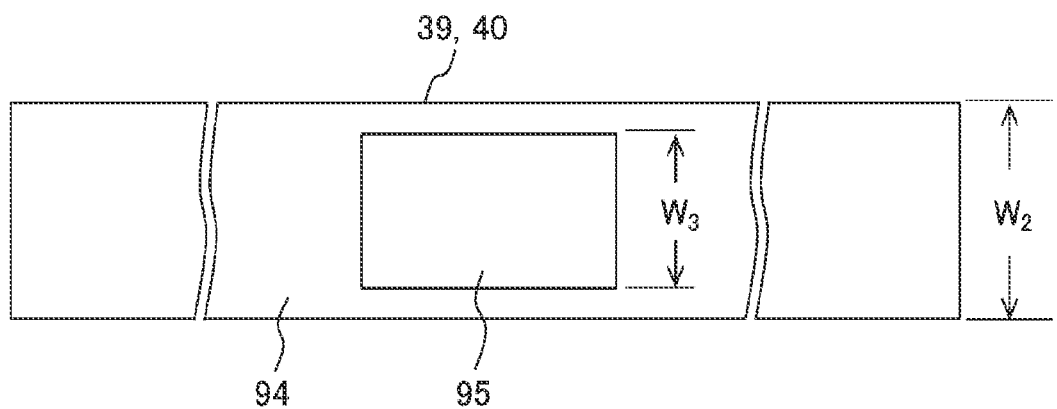
FIG. 6 is a plan view of an X-ray transmission plate illustrated in FIG. 4.

The movable floor 36 includes, as illustrated in FIG. 4, a number of footboards (footboard members) 38 made of metal (for example, made of a steel plate), and X-ray transmission plates (X-ray transmission members) 39 and 40. The movable floor 36 is disposed between the fixed-side ring rail 45A and the movable-side ring rail 45B. The movable floor 36 is a surrounding member formed by a number of footboards 38, the single X-ray transmission plate 39 and the single X-ray transmission plate 40 in a manner that they are freely bendable. The X-ray transmission plates 39 and 40 are separately disposed between the adjacent footboards 38 in the movable floor 36. The footboards 38 do not transmit the X-ray but the X-ray transmission plates 39 and 40 do. Each footboard 38 is a long and thin rectangular plate extending in the axis direction of the gantry 28, and has a width of $W_1$ in the circumference direction of the gantry 28 as illustrated in FIG. 5. Each of the X-ray transmission plates 39 and 40 is a long and thin rectangular plate extending in the axis direction of the gantry 28, and has a width of $W_2$ in the circumference direction of the gantry 28 as illustrated in FIG. 6. The width $W_2$ of each of the X-ray transmission plates 39 and 40 is larger than the width $W_1$ of the footboard 38. Each of the X-ray transmission plates 39 and 40 includes a metal plate 94 made of metal such as aluminum alloy and an X-ray transmission portion (X-ray transmission area) 95 that transmits the X-ray. The X-ray transmission portion 95 is, for example, a rectangular graphite plate and has a width of $W_3$ in the circumferential direction of the gantry 28. The width $W_3$ is larger than the width $W_1$ of the footboard 38 and smaller than the width $W_2$ of the X-ray transmission plates 39 and 40. The movable floor 36 includes footboard groups 74A, 74B, and 74C. The X-ray transmission plate 39 is disposed between the footboard group 74A and the footboard group 74C, and the X-ray transmission plate 40 is disposed between the footboard group 74B and the footboard group 74C. The X-ray transmission portion 95 is fitted into an opening, which is provided for the metal plate 94 and has the same size as the X-ray transmission portion 95, so as to be unified with the metal plate 94. The X-ray transmission portion 95 is surrounded by the metal plate 94. The X-ray transmission portion 95 can be formed of reinforced glass or plastic instead of graphite, and is formed of the non-metal material transparent to the X-ray, such as graphite, reinforced glass, or plastic (the non-metal material that easily transmits the X-ray). Alternatively, the X-ray transmission portion 95 may be omitted from the X-ray transmission plates 39 and 40 and instead, the X-ray transmission plates 39 and 40 may be formed of the non-metal material transparent to the X-ray (any of graphite, reinforced glass, and plastic).

In the footboard groups 74A, 74B, and 74C, a pair of wheels is rotatably attached to opposite ends of each footboard 38 in the longitudinal direction. The X-ray transmission plates 39 and 40 are provided with a pair of wheels at opposite ends thereof similarly. In a set of footboard groups 74A, 74B, and 74C, the adjacent footboards 38 are connected bendably at the opposite ends in the longitudinal direction of the footboard 38 (the wheels of the adjacent footboards 38 are connected with a link), and both sides of each footboard in the width direction is bent inward (see JP-H-11-47287-A, the paragraph [0018] and FIG. 4). The X-ray transmission plate 39 is also connected bendably to each of the adjacent footboard 38 included in the footboard group 74A and the adjacent footboard 38 included in the footboard group 74C. The X-ray transmission plate 40 is similarly connected bendably to each of the adjacent footboard 38 included in the footboard group 74B and the adjacent footboard 38 included in the footboard group 74C. An end 44B of each of the footboards 38 and the X-ray transmission plates 39 and 40 in the axis direction of the gantry 28 runs within the semi-cylindrical orbit 76 provided for the movable-side ring rail 45B. An end 44A of each of the footboards 38 and the X-ray transmission plates 39 and 40 in the axis direction of the gantry 28 runs within the semi-cylindrical orbit 76 provided for the fixed-side ring rail 45A.

Figure 2:
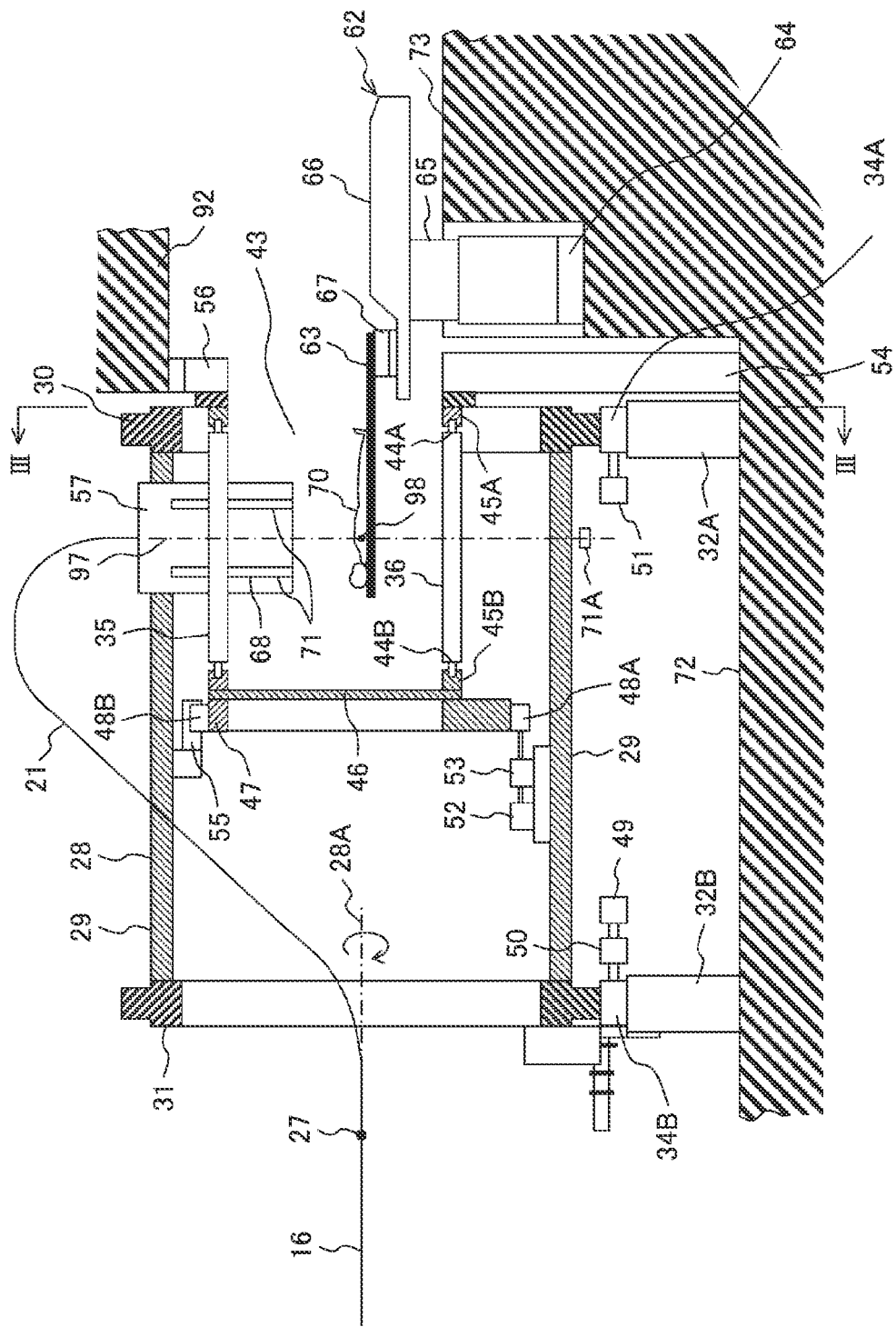
FIG. 2 is a magnified longitudinal sectional diagram of a gantry illustrated in FIG. 1.
Figure 3:
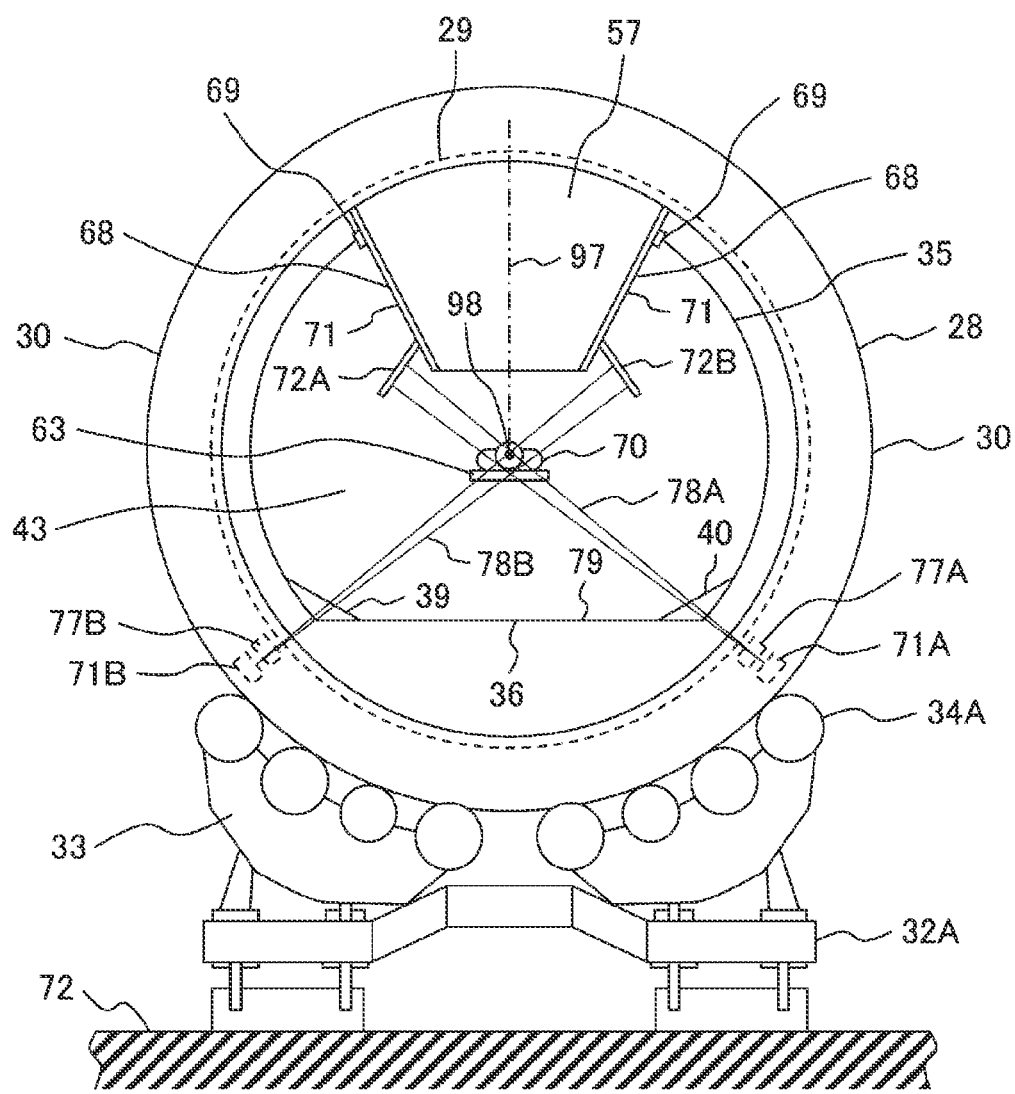
FIG. 3 is a diagram viewed from arrows III-III in FIG. 2.

As illustrated in FIG. 2, the fixed-side ring rail 45A is supported on a ceiling 92 of the building with a fixed supporter 56, and is further supported on the floor 72 with a fixed supporter 54. The movable-side ring rail 45B is supported by a plurality of support rollers 48B disposed along a circumferential direction of the rotary drum 29 on an inner surface of a support ring 55 disposed on an inner surface of the rotary drum 29 of the gantry 28. A ring rail driver 52 rotates the movable-side ring rail 45B in the direction opposite to the rotation of the gantry 28. The ring rail driver 52 is connected to one support roller 48A out of the support rollers 48B through a decelerator 53. The ring rail driver 52 and the decelerator 53 are installed on the inner surface of the rotary drum 29.

The irradiation system 57 rotates along with the rotation of the gantry 28 and driving of the ring rail driver 52 causes the support roller 48A to rotate the movable-side ring rail 45B in the opposite direction. If the gantry 28 is rotated in the opposite direction, the rotation of the support roller 48A by the driving of the ring rail driver 52 causes the movable-side ring rail 45B to rotate in the normal direction. Since the movable-side ring rail 45B rotates relative to the gantry 28, the movable-side ring rail 45B seems to stand still when viewed from a treatment room 43. As a result, even if the gantry 28 is rotated, the treatment cage 35 maintains the semi-cylindrical orbit 76 (the arc-like portion on the upper side and the horizontal portion on the lower side). That is to say, the movable floor 36 of the treatment cage 35 constantly constitutes a horizontal floor portion 79 without depending on the rotation angle of the gantry 28.

The movable floor 36 has enough rigidity, and will not deform even if the medical technician 93 works standing on the movable floor 36. The movable floor 36 offers a work space around the treatment stand 62.

In the footboard group 74C, a cover winding system 42 is installed between a pair of adjacent footboards 38. Upon the generation of the opening between the pair of footboards 38, the cover winding system 42 sends out the cover 41 to close the opening 75 (see FIG. 7). The cover winding system 42 may be configured in accordance with a known art, such as a winding pipe with the structure to maintain the tension, for example, roll screen or roll curtain.

Description will be made of a connector 68 between the irradiation system 57 and each end of the movable floor 36 (each of the footboard groups 74A and 74B) with reference to FIG. 4. The connector 68 includes a pair of slide members 69A and 69B and a pair of guide rails 71. The connector 68 is provided for each of a pair of side surfaces of the irradiation system 57 opposite to each other in the rotation direction of the gantry 28. The pair of slide members 69A and 69B is attached to one end of each of the footboard groups 74A and 74B. A pair of guide rails 71 as the guide members is installed on each of a pair of side surfaces of the irradiation system 57 opposite to each other in the rotating direction of the gantry 28. The slide members 69A and 69B attached to one end of the footboard group 74A are separately and movably attached to the pair of guide rails 71 installed on one side surface of the irradiation system 57. The slide members 69A and 69B attached to one end of the footboard group 74B are separately and movably attached to the pair of guide rails 71 installed on the other side surface of the irradiation system 57. As a result, the one end of each of the footboard groups 74A and 74B is connected to each of the pair of side surfaces of the irradiation system 57 by the connector 68 (the slide members 69A and 69B and a pair of guide rails 71) in a manner of being slidable in the radial direction of the gantry 28.

The irradiation system 57 has a shape tapering toward the center of rotation of the gantry 28. As a result, the pair of side surfaces of the irradiation system 57 opposite to each other in the rotating direction of the gantry 28 is inclined relative to the normal line of the rotation surface of the gantry 28.

The treatment room 43 is surrounded by the movable floor 36 of the treatment cage 35 within the rotary drum 29. The treatment room 43 is open on the front ring 30 side and closed by the back panel 46 on the rear ring 31 side. The irradiation system 57 is attached to the rotary drum 29 and extends toward the center of the rotary drum 29, and reaches the treatment room 43 formed more on the inside than the movable floor 36. The beam path 21 of the GABT 20 connected to the irradiation system 57 extends toward the rear ring 31 as illustrated in FIG. 2, and communicates with the beam path 16 of the HEBT 15 in the scramble portion 27 on the outside of the gantry 28. A center axis 28A of the gantry 28 (see FIG. 1 and FIG. 2) corresponds to the center of the rotation of the gantry 28 and goes along the center of the entrance of the beam path 21 in the scramble portion 27.

The treatment stand 62 includes, as illustrated in FIG. 2, a bed 63, an X-direction driving mechanism 64, a Y-direction driving mechanism 66, a vertical driving mechanism 65, and a rotation driving mechanism 67. These driving mechanisms are disposed outside the rotary drum 29. The X-direction driving mechanism 64 is installed in a treatment stand attachment area 73, which is higher than the floor 72. The X-direction driving mechanism 64 moves the bed 63 in a direction orthogonal to the rotating axis of the gantry 28. The vertical driving mechanism 65 is installed on the X-direction driving mechanism 64, the Y-direction driving mechanism 66 is installed on the vertical driving mechanism 65, and the rotation driving mechanism 67 is installed on the Y-direction driving mechanism 66. The bed 63 is installed on the rotation driving mechanism 67 and is supported by these driving mechanisms. The Y-direction driving mechanism 66 moves the bed 63 in a direction where the rotation axis of the gantry 28 extends. The rotation driving mechanism 67 rotates the bed 63 in a horizontal plane.

The treatment room 43 is formed by partitioning the space in the rotary drum 29 of the gantry 28 with the back panel 46, which serves as a partition wall. The treatment room 43 is set to the floor level near the rotation center of such a degree that the rotation radius of the gantry 28 is secured; thus, the treatment room 43 is set at a height of usually 6 to 8 m relative to the lowest position of the inner surface of the rotary drum 29. Therefore, the patient 70 on the bed 63 in the treatment stand 62 exists in the space at that height, and the treatment cage 35 forming the space surrounding the patient 70 therefore needs to be safe for the patient and the medical technician.

In order to obtain the image information of the target volume used to position the target volume before the target volume is irradiated with a particle beam and to confirm the position of the target volume during the irradiation with the particle beam, the particle therapy system 1 includes X-ray sources (X-ray generators) 71A and 71B and X-ray detection systems (such as flat panel detectors (FPD)) 72A and 72B. The X-ray detection systems 72A and 72B are provided for a pair of side surfaces of the irradiation system 57 opposite to each other in the circulating direction. The X-ray sources 71A and 71B are disposed at the center axis 97 of the irradiation system 57 in the axial direction of the gantry 28 (see FIG. 2). The X-ray detection systems 72A and 72B may be a semiconductor detector or a scintillator.

Figure 7:
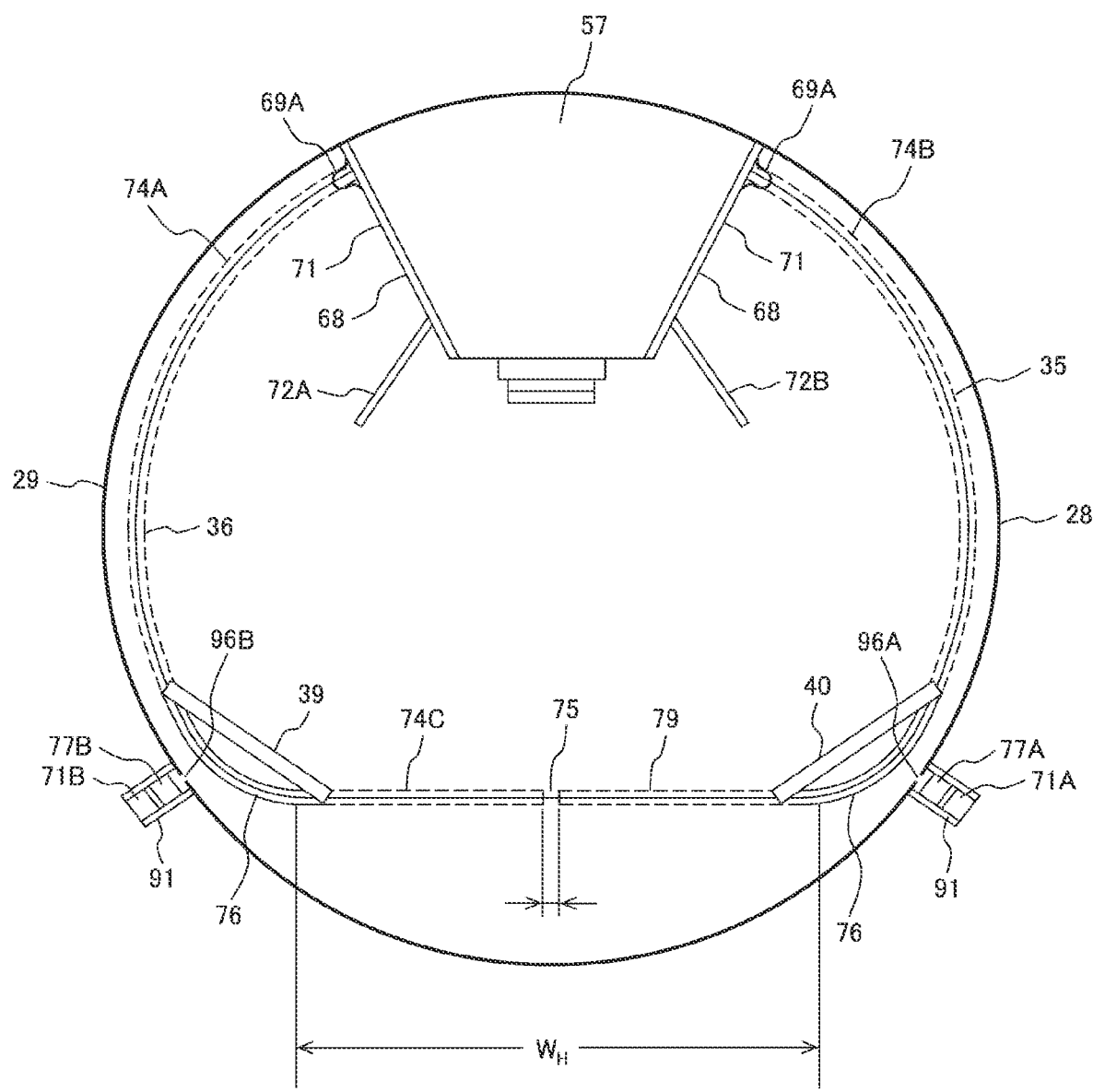
FIG. 7 is a diagram for describing the state of the movable floor of the radiation treatment cage when the rotation angle of the gantry illustrated in FIG. 2

The X-ray source 71A is installed on the outer surface of the rotary drum 29 of the gantry 28 by a supporter 91 as illustrated in FIG. 7. A collimator 77A is disposed on the outside of the rotary drum 29 in front of the X-ray source 71A and is attached to the supporter 91. The X-ray detection system 72A is disposed opposite to the X-ray source 71A and is attached to one side surface of the irradiation system 57 in the circulating direction as to receive an X-ray 78A emitted from the X-ray source 71A. At the position in the rotary drum 29 opposite to the X-ray source 71A, a penetration hole (X-ray transmission hole) 96A with the size to transmit the X-ray emitted from the X-ray source 71A is formed. In addition, the X-ray source 71A and the penetration hole 96A are disposed opposite to the X-ray transmission plate 40 included in the movable floor 36.

The X-ray source 71B is installed on the outer surface of the rotary drum 29 of the gantry 28 by the supporter 91 as illustrated in FIG. 7. A collimator 77B is disposed on the outside of the rotary drum 29 in front of the X-ray source 71B and is attached to the supporter 91. The X-ray detection system 72B is disposed opposite to the X-ray source 71B and is attached to the other side surface of the irradiation system 57 in the circulating direction as to receive an X-ray 78B emitted from the X-ray source 71B. At the position in the rotary drum 29 opposite to the X-ray source 71B, a penetration hole (X-ray transmission hole) 96B with the size to transmit the X-ray emitted from the X-ray source 71B is formed. In addition, the X-ray source 71B and the penetration hole 96B are disposed opposite to the X-ray transmission plate 39 included in the movable floor 36. The X-ray transmission portion 95 of the X-ray transmission plate 39 is disposed opposite to the X-ray source 71A. The X-ray transmission portion 95 of the X-ray transmission plate 40 is disposed opposite to the X-ray source 71B.

Each of the X-ray detection systems 72A and 72B is substantially configured to have 330 columns×330 rows of X-ray detectors (not illustrated) arranged on each of the planes thereof facing each of the X-ray transmission plates 39 and 40 (for example, the square plane with a length of approximately 50 cm on a side). The X-ray detector has, for example, a square X-ray incidence surface with a length of approximately 1.5 mm on a side (see JP-2006-239403-A, the paragraph [0027]).

Figure 11:
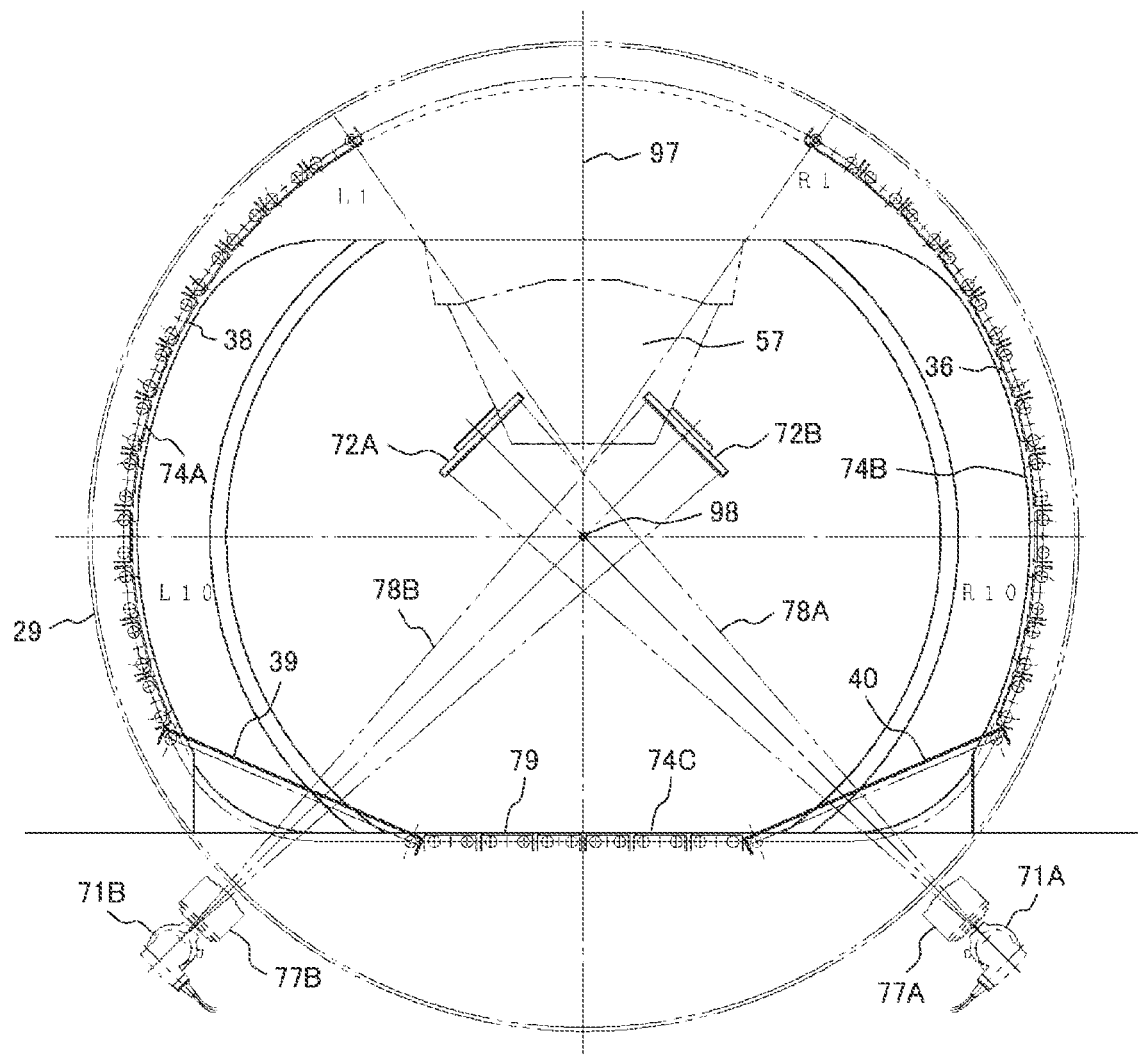
FIG. 11 is a diagram illustrating the positions of the X-ray transmission plates in the radiation treatment cage and the positions of the X-ray transmission on the X-ray transmission plates when the rotation angle of the gantry illustrated in FIG. 2

The angle between the line connecting an isocenter 98 and the hole (not illustrated) of the collimator 77A that transmits the X-ray and the line connecting the isocenter 98 and the hole (not illustrated) of the collimator 77B that transmits the X-ray is 90° (see FIG. 11). Therefore, the X-ray source 71A and the X-ray source 71B are disposed displaced by 90° in the circumferential direction of the gantry 28.

The function of the X-ray sources 71A and 71B and the X-ray detection systems 72A and 72B is described based on an example of positioning the target volume before the target volume is irradiated with an ion beam. In this embodiment, the target volume of the patient 70 lying on the bed 63 is positioned by the method according to JP-2006-239403-A.

The bed 63 on which the patient 70 lies down is moved by the driving of the X-direction driving mechanism 64, the Y-direction driving mechanism 66, the vertical driving mechanism 65, and the rotation driving mechanism 67; thus, the target volume of the patient 70 is roughly positioned relative to the irradiation system 57. On this occasion, the rotation angle of the gantry 28 is, for example, 0° and the irradiation system 57 extends downward. While the gantry 28 is rotated, the current X-ray computed tomography is carried out. In this current X-ray computed tomography, while the gantry 28 is rotated, the X-rays 78A and 78B are delivered to the target volume of the patient 70 from the X-ray sources 71A and 71B, respectively. The X-ray 78A emitted from the X-ray source 71A passes through the collimator 77A and the penetration hole 96A and further through the X-ray transmission portion 95 of the X-ray transmission plate 40, and then delivered to the target volume. The X-ray 78A having transmitted through the target volume is detected by each X-ray detector of the X-ray detection system 72A. The X-ray 78B emitted from the X-ray source 71B passes through the collimator 77B and the penetration hole 96B and further through the X-ray transmission portion 95 of the X-ray transmission plate 39, and then delivered to the target volume. The X-ray 78B having transmitted through the target volume is detected by each X-ray detector of the X-ray detection system 72B. The irradiation of the target volume with the X-rays 78A and 78B from the X-ray sources 71A and 71B is carried out while the gantry 28 is rotated. In this case, the gantry 28 is rotated by, for example, 275° because the X-ray source 71A and the X-ray source 71B are displaced by 90° in the circumferential direction of the gantry 28. By rotating the gantry 28 by 275° while the X-rays are emitted from the X-ray sources 71A and 71B, the X-ray can be delivered to the target volume of the patient 70 on the bed 63 from 360° around the patient 70.

Each X-ray detector of the X-ray detection system 72A having detected the X-ray 78A outputs the X-ray detection signal. The X-ray detection signal output from each X-ray detector is input to a signal processor (not illustrated) connected to each X-ray detector of the X-ray detection system 72A, and each signal processor accumulates the X-ray detection signals to provide the X-ray intensity information at every set time interval. Each X-ray detector of the X-ray detection system 72B having detected the X-ray 78B also outputs the X-ray detection signal. The X-ray detection signal output from the X-ray detector is input to a signal processor (not illustrated) connected to every X-ray detector of the X-ray detection system 72B, and each signal processor accumulates the X-ray detection signals to provide the X-ray intensity information at every set time interval.

To an image information formation system (tomographic information formation system) (not illustrated), the X-ray intensity information for every X-ray detector of the X-ray detection system 72A, the X-ray intensity information for every X-ray detector of the X-ray detection system 72B, and the rotation angle of the gantry 28 measured with the angle detector 51 are input. Based on the X-ray intensity information and the measured rotation angles of the gantry 28, the image information formation system forms the tomographic information (current tomographic information) including the target volume of the patient 70 (see JP-2006-239403-A, the paragraph [0037]). The formed current tomographic information is input to a positioning data generation system (not illustrated). To the positioning data generation system, three-dimensional tomographic information (reference tomographic information) obtained by the X-ray computed tomography (reference X-ray computed tomography) prepared in advance has already been input and stored in the memory (not illustrated). Based on the current tomographic information and the reference tomographic information, the positioning data generation system calculates the amount of movement of the bed 63 in the X direction and the Y direction, corresponding to the bed positioning data in the X-Y plane, the rotation angle of the bed 63, and the amount of movement of the bed 63 in the Z direction, corresponding to the bed positioning data in the X-Z plane (see JP-2006-239403-A, the paragraphs [0040]-[0044]).

A bed controller (not illustrated) controls the corresponding driving mechanism for the treatment stand 62 on the basis of the input amount of movement of the bed 63 in the X direction, Y direction, and Z direction and the rotation angle of the bed 63, thereby moving the bed 63 (see JP-2006-239403-A, the paragraph [0045]). In this manner, the target volume of the patient 70 on the bed 63 is moved to the position coinciding with the isocenter 98 located at the intersection between the center axis 97 of the irradiation system 57 and the center axis 28A of the gantry 28, and thus the positioning of the target volume is completed. After the positioning of the target volume is completed, the target volume is irradiated with the particle beam in the particle therapy system 1 to treat the target volume with the particle beam.

Description is made of the summary of the irradiation of the target volume of the patient 70 with the particle beam, such as a proton beam (or carbon beam). The gantry 28 can be rotated by 360° around the patient 70 on the bed 63. Before the target volume is irradiated with the proton beam (hereinafter simply referred to as ion beam), the rotation system 49 is driven to rotate the gantry 28 so that the center axis 97 of the irradiation system 57 coincides with the irradiation direction of the ion beam according to the treatment plan. The gantry 28 is rotated at a speed of 1 $\text{min}^{-1}$. Whether the center axis 97 of the irradiation system 57 has coincided with the irradiation direction of the ion beam is checked based on the rotation angle of the gantry 28 measured with the angle detector 51.

In order to turn the irradiation system 57 to the irradiation direction of the ion beam by rotating the gantry 28, the movable-side ring rail 45B is rotated in the direction opposite to the rotation of the gantry 28 by the driving of the ring rail driver 52. This makes the movable-side ring rail 45B look like it stands still. Therefore, as the irradiation system 57 is turned by the rotation of the gantry 28, the movable floor 36 with its opposite ends attached movably to a pair of guide rails 71 on a pair of opposite side surfaces of the irradiation system 57 with the slide members 69A and 69B moves along the semi-cylindrical orbit 76.

The gantry 28 having rotated to the set rotation angle is stopped. Then, the ion (for example, proton) generated in the ion source is incident into the linear accelerator 14 and then accelerated therein. The ion beam emitted from the linear accelerator 14 is incident into the circular beam duct 4 of the synchrotron accelerator 3 through the injector 5. While circulating in the beam duct 4, the ion beam is accelerated until having the set energy (for example, 200 MeV) required to reach the deepest layer among a plurality of layers of the target volume in the ion beam irradiation direction. The energy of the ion beam used to treat the target volume is usually in the range of 100 to 200 MeV, and is set in accordance with the depth of the target volume from the surface of the body.

With the scanning magnets 58 and 59, the irradiation point of the ion beam within the layer is set. The opening/closing switch 12 is closed and the radiofrequency voltage from the radiofrequency power source 11 is applied from the extraction radiofrequency electrode 10 to the ion beam circulating in the beam duct 4. As a result, the circulating ion beam is emitted from the synchrotron accelerator 3 to the beam path 16 through the septum magnet 13. The emitted ion beam reaches the irradiation system 57 through the beam paths 16 and 21. The ion beam having reached to the inside of the irradiation system 57 is delivered to the irradiation point of the ion beam of the target volume in the layer, which has been set by the scanning magnets 58 and 59.

While the target volume is irradiated with the ion beam in the state that the center axis 97 of the irradiation system 57 is aligned in a predetermined irradiation direction of the ion beam, the X-ray 78A emitted from the X-ray source 71A and the X-ray 78B emitted from the X-ray source 71B are delivered to the target volume of the patient 70 on the bed 63. The X-ray 78A having transmitted through the patient 70 is detected by each X-ray detector of the X-ray detection system 72A, and the X-ray 78B having transmitted through the patient 70 is detected by each X-ray detector of the X-ray detection system 72B.

In a manner similar to the aforementioned positioning of the target volume, the signal processor connected to each X-ray detector of the X-ray detection system 72A obtains the X-ray intensity information on the basis of the X-ray detection signal from the X-ray detector. The image information formation system forms the primary two-dimensional image information of the target volume in the plane orthogonal to the radiation direction of the X-ray 78A from the X-ray source 71A on the basis of the X-ray intensity information obtained with each signal processor and the measured rotation angle of the gantry 28. The plane orthogonal to the radiation direction of the X-ray 78A from the X-ray source 71A corresponds to the plane orthogonal to the direction to the center axis 28A of the gantry 28 at an angle obtained by adding 135° to the measured rotation angle of the gantry 28 (the angle of center axis 97 of the irradiation system 57).

In a manner similar to the aforementioned formation of the primary two-dimensional image information, the image information formation system forms the secondary two-dimensional image information of the target volume in the plane orthogonal to the radiation direction of the X-ray 78B from the X-ray source 71B on the basis of the X-ray intensity information obtained with each signal processor connected to each X-ray detector of the X-ray detection system 72B and the measured rotation angle of the gantry 28. The plane orthogonal to the radiation direction of the X-ray 78B from the X-ray source 71B corresponds to the plane orthogonal to the direction to the center axis 28A of the gantry 28 at an angle obtained by adding 225° to the measured rotation angle of the gantry 28 (the angle of the center axis 97 of the irradiation system 57).

Based on the primary two-dimensional image information and the secondary two-dimensional image information, the size and shape of the target volume can be known in the irradiation with the ion beam. In addition, based on how the size and shape of the target volume have changed since the start of the irradiation of the target volume with the ion beam, the effect of the treatment by the irradiation with the ion beam can be known.

Moreover, the primary two-dimensional image information and the secondary two-dimensional image information formed by the image information formation system are input to the positioning data generation system, and the positioning data generation system calculates the amount of displacement of the target volume irradiated with the ion beam from the reference tomographic information on the basis of the reference tomographic information, the primary two-dimensional image information and the secondary two-dimensional image information. Based on the calculated amount of displacement, the position of the target volume currently irradiated with the ion beam can be known.

Description is hereinafter made of the operation of the connector 68 including the slide members 69A and 69B and the pair of guide rails 71, which connects between the irradiation system 57 and each of the footboard groups 74A and 74B.

FIG. 7 illustrates the sectional shape of the movable floor 36 of the treatment cage 35 when the irradiation system 57 is right above the bed 63. In the state illustrated in FIG. 7, the rotation angle of the gantry 28 is 0°. The slide members 69A and 69B attached movably to the pair of guide rails 71 provided for each of the pair of side surfaces of the irradiation system 57 opposite to each other in the rotating direction of the gantry 28 and attached to one end of each of the footboards 74A and 74B are in the farthest position from the center axis 28A of the gantry 28 in the radial direction of the gantry 28.

Figure 8:
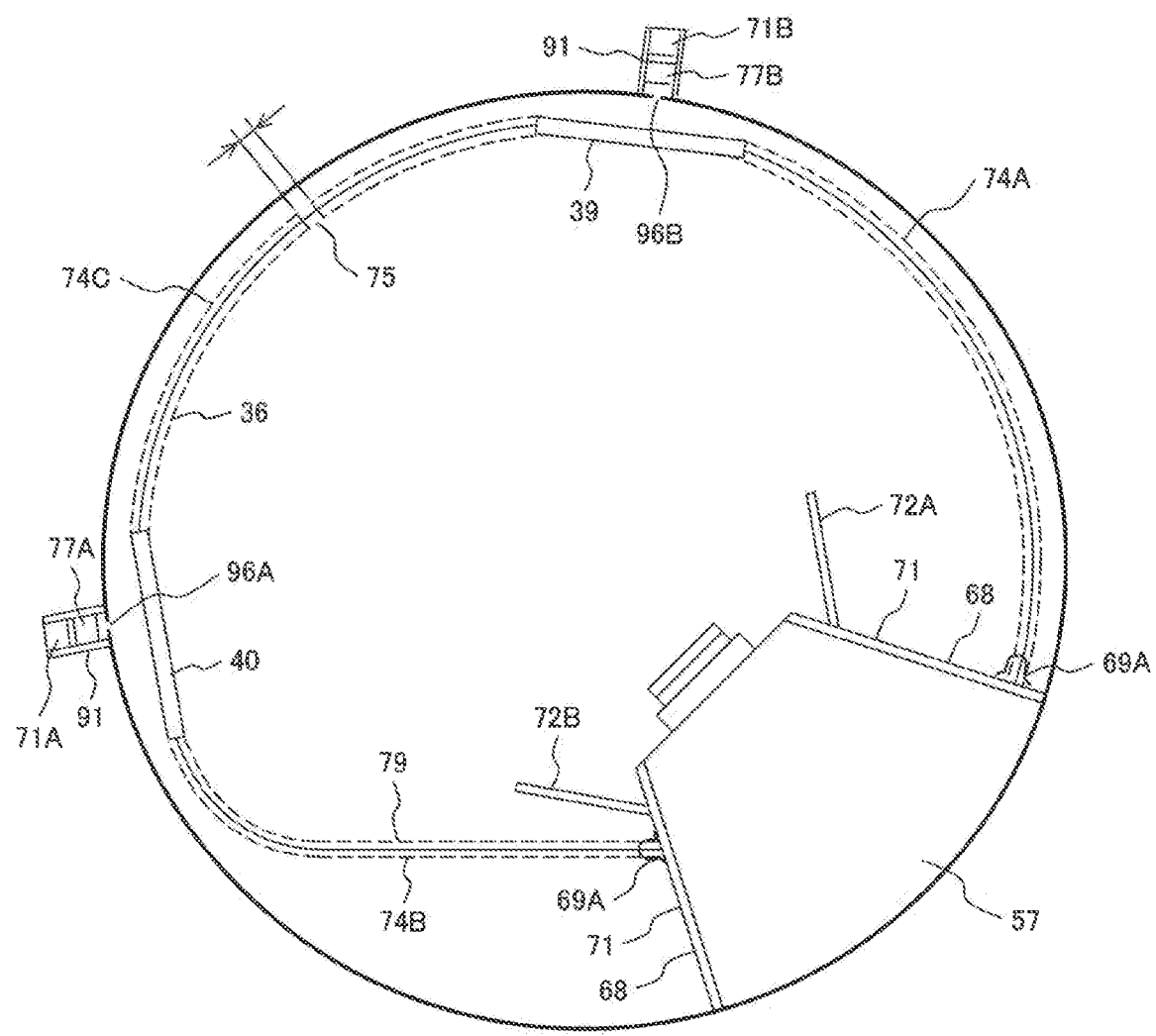
FIG. 8 is a diagram for describing the state of the movable floor of the radiation treatment cage when the rotation angle of the gantry illustrated in FIG. 2
Figure 9:
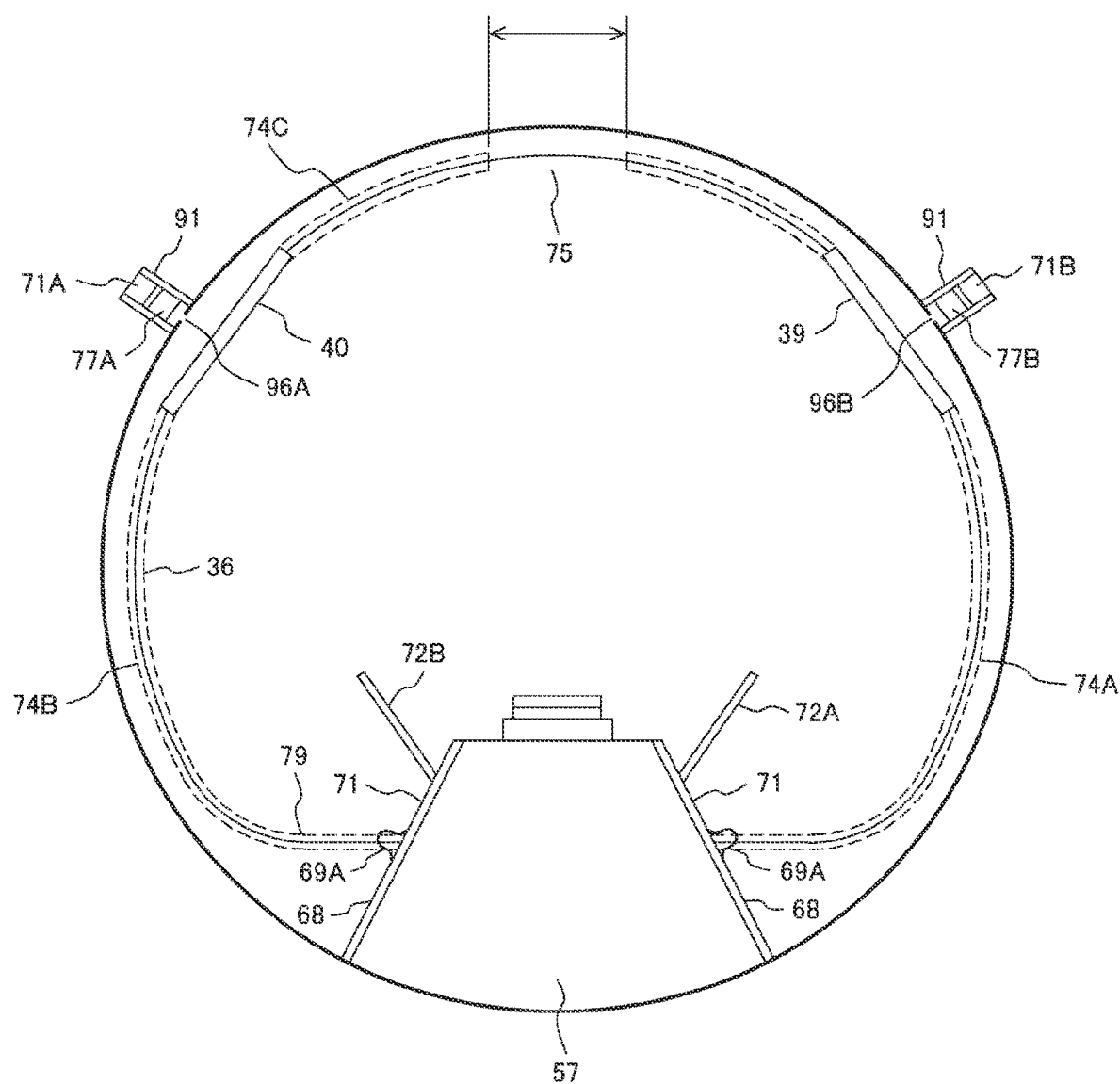
FIG. 9 is a diagram for describing the state of the movable floor of the radiation treatment cage when the rotation angle of the gantry illustrated in FIG. 2

Between the pair of footboards 38 in the footboard group 74C, the cover winding system 42 is installed. Synchronizing with the generation of the opening 75 between the pair of footboards 38, the cover winding system 42 sends out the cover 41 so as to close the opening 75 (see FIG. 7). This opening 75 exists right below the bed 63 (at the position where the rotation angle of the gantry 28 is 180°). Note that the opening 75 is closed by the cover 41 but this is not illustrated in FIG. 7 for the convenience of description. Neither FIG. 8 nor FIG. 9 illustrates the cover 41.

Here, the concept of the inner wall length defined in this embodiment is described. The irradiation system 57 circulates around the rotation axis of the gantry 28 as the gantry 28 rotates. Meanwhile, the semi-cylindrical orbit 76 which is provided for each of the fixed-side ring rail 45A and the movable-side ring rail 45B of the treatment cage 35 and which guides the movable floor 36 stands still. Needless to say, the total length of each semi-cylindrical orbit 76 is constant (unchanged) in the treatment cage 35. Along the length of the semi-cylindrical orbit 76, which is the length excluding the length corresponding to the irradiation system 57 (the length of the irradiation system 57 between the slide members 69A attached movably to the guide rails 71 on the pair of side surfaces of the irradiation system 57 opposite to each other in the rotating direction of the gantry 28) from the entire length of the semi-cylindrical orbit 76, the arc-like portion and the horizontal portion are formed. Of the semi-cylindrical orbit 76, the length of the arc-like portion and the horizontal portion is defined as the inner wall length. That is to say, the inner wall length corresponds to the difference between the entire length of the semi-cylindrical orbit 76 and the length corresponding to the irradiation system 57. On the other hand, the inner wall length substantially corresponds to the total of the lengths of the footboard groups 74A, 74B, and 74C, the widths of the X-ray transmission plates 39 and 40, and the length of the opening 75.

While the irradiation system 57 is right above the bed 63, each of the X-ray transmission plates 39 and 40 exists near the connecting portion of the semi-cylindrical orbit 76.

If the orbit for guiding the movable floor 36, which is provided for each of the fixed-side ring rail 45A and the movable-side ring rail 45B of the treatment cage, is a circular orbit, the inner wall length is constant not depending on the rotation angle of the gantry 28. However, since the orbit 76 provided for each of the fixed-side ring rail 45A and the movable-side ring rail 45B is semi-cylindrical, the inner wall length is different depending on the rotation angle of the gantry 28. That is to say, since the length corresponding to the irradiation system 57 is different depending on the rotation angle of the gantry 28, the inner wall length is different depending on the rotation angle.

If the irradiation system 57 is present at the arc-like portion of the semi-cylindrical orbit 76 (if the gantry 28 is rotated by the angle ranging from 0° to 90°), the length corresponding to the irradiation system 57 is constant and the inner wall length is constant. As a part of the irradiation system 57 is moved to the connecting portion of the semi-cylindrical orbit 76 (the rotation angle of the gantry 28 ranges from 90° to 120°) and then to the horizontal portion (the rotation angle of the gantry 28 ranges from 120° to 180°), the length corresponding to the irradiation system 57 is changed and the inner wall length is changed.

For example, when the rotation angle of the gantry 28 is 180° and the irradiation system 57 is in the horizontal portion (see FIG. 9), the slide members 69A and 69B attached movably to the pair of guide rails 71 disposed on each of the pair of side surfaces of the irradiation system 57 opposite to each other in the rotating direction of the gantry 28 and attached to one end of each of the footboard groups 74A and 74B are both in the closest position to the center axis 28A of the gantry 28 in the radial direction of the gantry 28. Here, the length of the irradiation system 57 (the length corresponding to the irradiation system 57) between the slide member 69A attached to one end of the footboard group 74A and the slide member 69A attached to one end of the footboard group 74B is shorter than the length of the irradiation system 57 between the slide member 69A attached to one end of the footboard group 74A and the slide member 69A attached to one end of the footboard group 74B in the state that the irradiation system 57 is in the arc-like portion with the gantry 28 having a rotation angle of 0° (see FIG. 7).

When the movable floor 36 is moved along the semi-cylindrical orbit 76 in accordance with the rotation angle of the gantry 28, the slide members 69A and 69B separately attached movably to the pair of guide rails 71 disposed on the pair of side surfaces of the irradiation system 57 opposite to each other in the rotating direction of the gantry 28 are moved along with the movement of the movable floor 36, i.e., along the guide rail 71 in the radial direction of the gantry 28 as the irradiation system 57 turns.

While the irradiation system 57 is in the arc-like portion of the semi-cylindrical orbit 76 (for example, the rotation angle of the gantry 28 ranges from 0° to 90°), the pair of slide members 69A and 69B is in the farthest position from the center axis 28A of the gantry 28 in the radial direction of the gantry 28. As a part of the irradiation system 57 is moved to the connecting portion of the semi-cylindrical orbit 76 (the rotation angle of the gantry 28 ranges 90° to 120°) and then to the horizontal portion of the orbit 76 (the rotation angle of the gantry 28 ranges from 120° to 180°), the slide members 69A and 69B attached to one end of the footboard group 74B move closer to the center axis 28A of the gantry 28 along the pair of guide rail 71 disposed on one side surface on the turning-direction side of the irradiation system 57 as the irradiation system 57 turns (FIG. 8). While the entire irradiation system 57 is in the horizontal portion of the semi-cylindrical orbit 76 (the rotation angle of the gantry 28 ranges from 150° to 180°), the slide members 69A and 69B attached to one end of the footboard group 74A move closer to the center axis 28A of the gantry 28 along the pair of guide rail 71 disposed on the other side surface opposite to the turning-direction side of the irradiation system 57 as the irradiation system 57 turns (FIG. 9). When the irradiation system 57 approaches to the area right below the bed 63 (the rotation angle of the gantry 28 is 180°), the slide members 69A and 69B move closer to the guide rails 71 on both side surfaces of the irradiation system 57 as the irradiation system 57 turns.

That is to say, the change in inner wall length depending on the rotation angle of the gantry 28 is synchronized with the change in length of the opening 75 and the movement of the slide members 69A and 69B along the guide rail 71. Other specific examples than the example illustrated in FIG. 7 are described with reference to FIG. 8 and FIG. 9.

FIG. 8 illustrates the state of the movable floor 36 of the treatment cage 35 when the irradiation system 57 is at the position where the rotation angle of the gantry 28 is 135°. A part of the irradiation system 57 is in the horizontal portion of the semi-cylindrical orbit 76. In this state, the slide members 69A and 69B attached to one end of the footboard group 74B move closer to the center axis 28A of the gantry 28 in the radial direction of the gantry 28, and the slide members 69A and 69B attached to one end of the footboard group 74A is in the farthest position from the center axis 28A of the gantry 28 in the radial direction of the gantry 28. At this time, the inner wall length is the shortest and the length of the opening 75 is also the shortest. The length of the portion of the movable floor 36 (this portion is hereinafter referred to as a first movable floor portion) from the slide members 69A and 69B to the opening 75 on the footboard group 74A side and the length of the portion of the movable floor 36 (this portion is hereinafter referred to as a second movable floor portion) from the slide members 69A and 69B to the opening 75 on the footboard group 74B side are set so that the first movable floor portion and the second movable floor portion do not interfere with each other when the inner wall length is the shortest, i.e., so that the opening 75 has a length of 0 or more. The first movable floor portion includes the X-ray transmission plate 39 and the second movable floor portion includes the X-ray transmission plate 40.

FIG. 9 illustrates the state of the movable floor 36 of the treatment cage 35 when the irradiation system 57 is at the position where the rotation angle of the gantry 28 is 180°. The entire irradiation system 57 is present in the horizontal portion of the semi-cylindrical orbit 76. The slide members 69A and 69B attached to one end of each of the footboard groups 74A and 74B move toward the center of the pair of guide rails 71 provided on the circulating-direction side and opposite to the circulating-direction side of the irradiation system 57 as the movable floor 36 moves along the semi-cylindrical orbit 76. On this occasion, the length of the opening 75 is the maximum. The opening 75 is right above the bed 63 (at the position corresponding to a rotation angle of 0°).

Next, description is made of the safe approach of the medical technician 93 to the patient 70 at every rotation angle of the gantry 28, focusing on the change in position and length of the opening 75 depending on the rotation angle of the gantry 28. While the irradiation system 57 is at the position where the gantry 28 has a rotation angle of 0°), the opening 75 is at the position corresponding to a rotation angle of 180°, i.e., right below the bed 63 (see FIG. 7). Therefore, the opening 75 does not lead to a safety problem. While the irradiation system 57 is present at the position where the rotation angle of the gantry 28 ranges from 0° to 60°, the opening 75 is generated in the horizontal floor portion 79 of the movable floor 36 and the horizontal floor portion 79 is formed by the footboard group 74C. However, the structure with the inclination (tapered shape) of the irradiation system 57 as described below provides the effect that enables the opening 75 to maintain the very small length; thus, the opening 75 does not lead to the safety problem. In addition, the opening 75 is closed by the cover 41, thereby preventing the medical technician 93 and the patient 70 from feeling anxiety.

While the irradiation system 57 is present at the position where the rotation angle of the gantry 28 ranges from 60° to 180°, the opening 75 is not generated in the horizontal floor portion 79 of the movable floor 36. Thus, the opening 75 does not lead to the safety problem. In particular, when the irradiation system 57 is at the position where the rotation angle of the gantry 28 is 135°, the length of the opening 75 is the shortest (substantially 0 in this embodiment) (see FIG. 8). When the irradiation system 57 is at the position where the rotation angle of the gantry 28 is 180°, the length of the opening 75 is the maximum but the opening 75 is at the position corresponding to a rotation angle of 0°, i.e., right above the bed 63 (see FIG. 9), in which case the safety problem is not concerned. In this regard, the opening 75 is closed by the cover 41, so that people do not feel anxiety.

In this manner, in this embodiment, the medical technician 93 can stand on the horizontal floor portion 79 of the movable floor 36 and approach the patient 70 safely without depending on the rotating angle of the gantry 28.

To help the understanding of the operation, the numerals of the rotation angles of the gantry 28 are illustrated as examples and may vary depending on the size of the semi-cylindrical orbit 76 and the size of the irradiation system 57. In addition, the operation when the irradiation system 57 is present at the position where the rotation angle of the gantry 28 ranges from 0° to 180° has been described, and the operation when the irradiation system 57 is present at the position where the rotation angle of the gantry 28 ranges from 180° to 360° is omitted because the treatment cage 35 is horizontally symmetric.

In this embodiment, the orbit 76 including the arc-like portion and the horizontal portion connected to opposite ends of the arc-like portion is provided for each of the fixed-side ring rail 45A and the movable-side ring rail 45B. Thus, the movable floor 36 moving along this orbit 76 forms the horizontal floor portion 79 in the horizontal portion of the orbit 76. The medical technician 93 can stand on the horizontal floor portion 79 and easily access (for example, perform medical act on) the patient 70 on the bed 63 inserted into the treatment room 43.

The X-ray sources 71A and 71B are attached to the rotary drum 29 of the gantry 28, and the X-ray detection systems 72A and 72B are attached to the irradiation system 57 opposite to the X-ray sources 71A and 71B, respectively. This configuration eliminates the necessity of moving the X-ray sources 71A and 71B and the X-ray detection systems 72A and 72B in the axial direction of the gantry 28 in the X-raying of the target volume in order to position the target volume or the like. Thus, the time required to start the X-raying can be shortened. This can improve the treatment throughput. In this X-raying, the X-rays 78A and 78B emitted from the X-ray sources 71A and 71B can be delivered to the patient 70 on the bed 63 though the X-ray transmission plates 40 and 39 provided for the movable floor 36, respectively.

In the particle therapy system according to JP-2006-239403-A, however, the irradiation system is provided with the X-ray source (X-ray tube); therefore, the position of the target volume cannot be checked while the target volume is irradiated with the ion beam. In the particle therapy system 1 according to this embodiment, on the other hand, the X-ray sources 71A and 71B are attached to the gantry 28. This configuration enables to irradiate the target volume in two different directions with the X-rays 78A and 78B emitted from the X-ray sources 71A and 71B, respectively, while the target volume is irradiated with the ion beam. In addition, the X-rays 78A and 78B having transmitted through the target volume can be detected by the X-ray detection systems 72A and 72B. With the X-ray detection signals output from the X-ray detectors of the X-ray detection systems 72A and 72B, the tomographic information of the target volume of the patient 70 on the bed 63 who is irradiated with the ion beam from the irradiation system 57 can be formed. With the use of this tomographic information, the position of the target volume irradiated with the ion beam can be known. Since the X-rays 78A and 78B are delivered to the target volume from the two different directions, the position of the target volume irradiated with the ion beam can be known with high accuracy. In addition, by using the tomographic information, the change in size of the target volume irradiated with the ion beam can be known, and the treatment effect by the irradiation with the ion beam can be known.

The X-ray sources 71A and 71B and the collimators 77A and 77B may be attached to the inner surface of the rotary drum 29 and disposed outside the movable floor 36. The thusly arranged X-ray sources 71A and 71B and the like can provide the positioning data of the target volume, and makes it possible to know the position of the target volume irradiated with the ion beam and the change in size of the target volume irradiated with the ion beam.

In this embodiment, the X-ray sources 71A and 71B are attached to the outer surface of the rotary drum 29 of the gantry 28. This configuration can reduce the space formed between the movable floor 36 and the inner surface of the rotary drum 29 and reduce the diameter of the gantry 28, as compared to the case in which the X-ray sources 71A and 71B are attached to the inner surface of the rotary drum 29. Thus, the gantry 28 can be reduced in size.

The X-ray 78A emitted from the X-ray source 71A attached to the outer surface of the rotary drum 29 is delivered to the target volume of the patient 70 through the penetration hole 96A provided for the rotary drum 29 and through the X-ray transmission portion 95 of the X-ray transmission plate 40. Thus, the emitted X-ray 78A can be delivered to the patient 70 without being blocked. This can provide the clear image of and near the target volume with the use of the compact X-ray source 71A. The X-ray 78B emitted from the X-ray source 71B attached to the outer surface of the rotary drum 29 is delivered to the target volume of the patient 70 through the penetration hole 96B provided for the rotary drum 29 and through the X-ray transmission portion 95 of the X-ray transmission plate 39. Thus, the X-ray 78B emitted from the X-ray source 71B also provides the similar effect.

It is necessary to make the center axis 97 of the irradiation system 57 coincide with the irradiation direction of the ion beam formed by the treatment plan. The particle therapy system 1 is configured to deliver the ion beam to the target volume from around in the range of substantially 0° to 360°. The present inventors have found that, when the target volume is irradiated with the X-ray from around the target volume, the positions on the X-ray transmission plates 40 and 39 where the X-rays 78A and 78B emitted from the X-ray sources 71A and 71B transmit vary depending on the rotation angle of the gantry 28. How the transmission position changes is described with reference to FIG. 11, FIG. 12, and FIG. 13.

Figure 12:
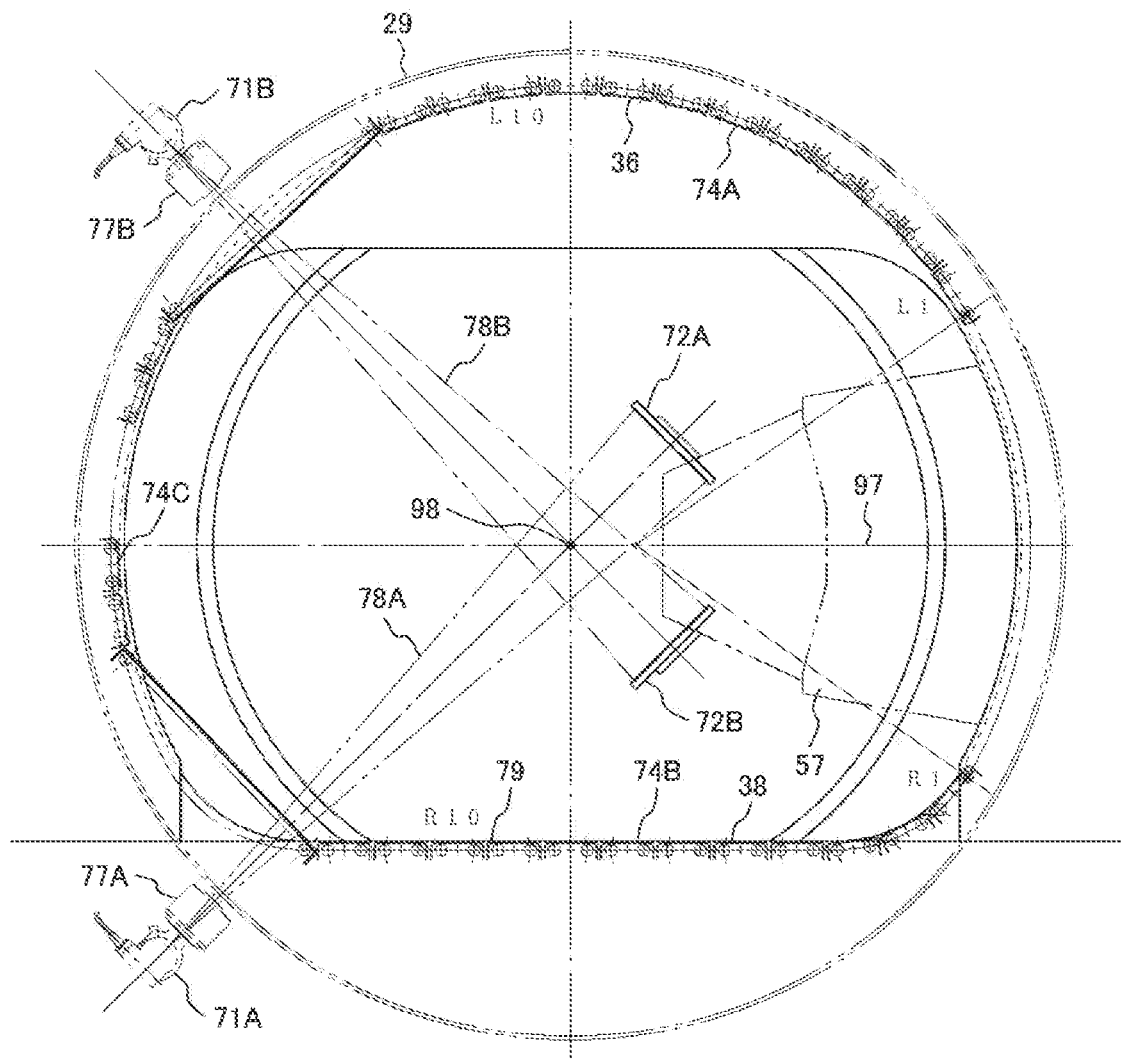
FIG. 12 is a diagram illustrating the positions of the X-ray transmission plates in the radiation treatment cage and the positions of the X-ray transmission on the X-ray transmission plates when the rotation angle of the gantry illustrated in FIG. 2
Figure 13:
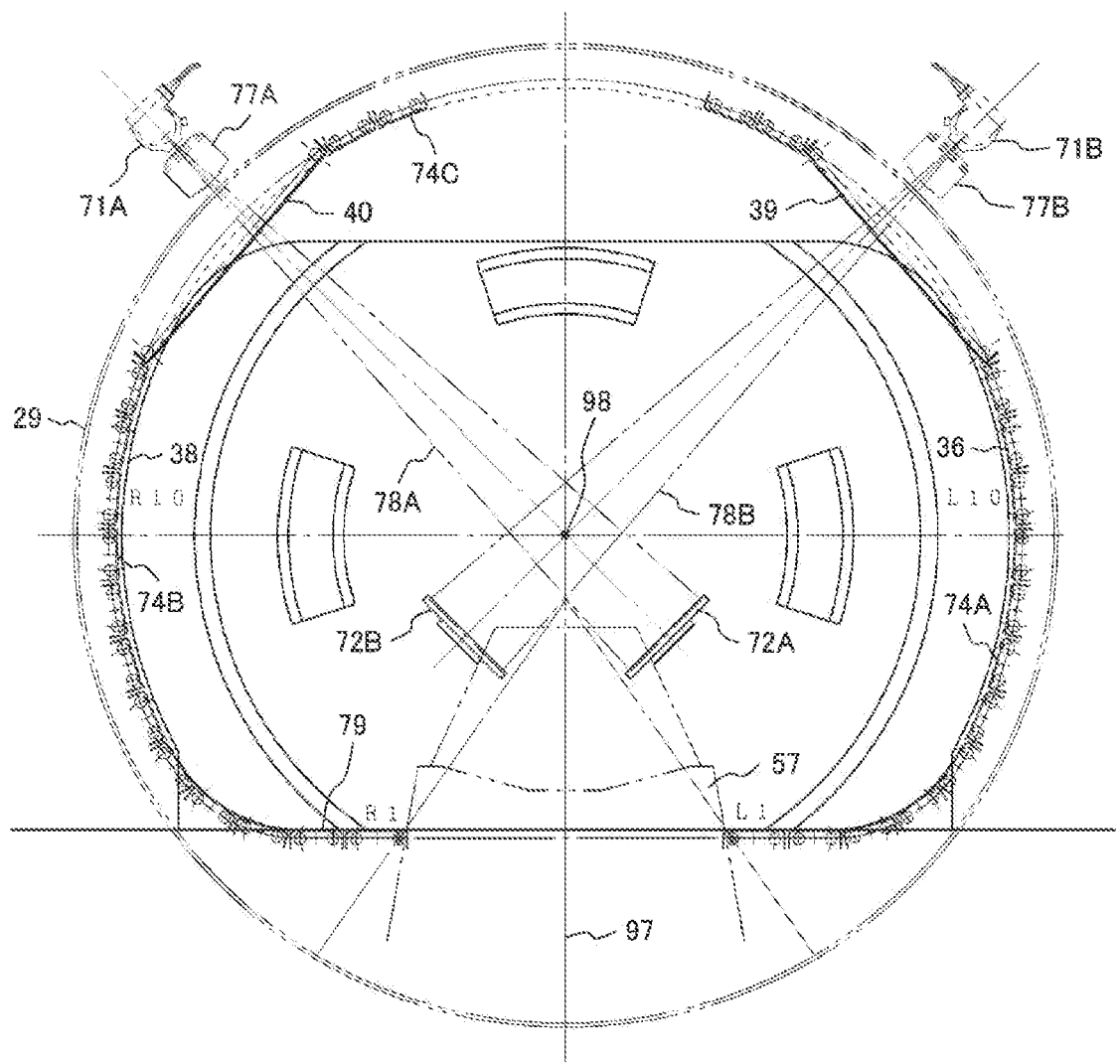
FIG. 13 is a diagram illustrating the positions of the X-ray transmission plates in the radiation treatment cage and the positions of the X-ray transmission on the X-ray transmission plates when the rotation angle of the gantry illustrated in FIG. 2

FIG. 11 illustrates the position of each X-ray transmission plate and the position of the X-ray transmission on the X-ray transmission plate in the treatment cage when the rotation angle of the gantry is 0°, FIG. 12 illustrates those positions when the rotation angle of the gantry is 90°, and FIG. 13 illustrates those positions when the rotation angle of the gantry is 180°. As the movable floor 36 is moved along the orbit 76 along with the rotation of the gantry 28, the X-ray transmission plates 39 and 40 of the movable floor 36 are also moved along the orbit 76 smoothly. Along with this, the positions of the X-ray transmission plates 39 and 40 in the orbit 76 change according to the rotation angle of the gantry 28. In addition, the positions on the X-ray transmission plates 39 and 40 where the X-rays 78A and 78B transmit also vary in the circumferential direction of the gantry 28 in accordance with the rotation angle of the gantry 28 as illustrated in FIG. 11, FIG. 12, and FIG. 13. Since the rotation of the gantry 28 thusly changes the transmission position of the X-ray on each of the X-ray transmission plates 39 and 40, the width $W_3$ of the X-ray transmission portion 95 in the circumferential direction of the gantry 28 needs to be larger than the width $W_1$ of the footboard 38. As the horizontal portion of the semi-cylindrical orbit 76 has a width of $W_H$, the horizontal floor portion 79 of the movable floor 36 formed by this horizontal portion also has a width of $W_H$. The horizontal floor portion 79 needs to be formed in order to enable the medical technician 93 to approach the patient on the bed 63 to conduct the treatment in the treatment room 43 safely. For these reasons, the X-ray transmission plates 39 and 40 need to have the width $W_2$ that is less than or equal to $W_H-W_1$ ($\geq W_2$).

The treatment cage according to JP-2011-156263-A (hereinafter referred to as the conventional treatment cage, simply) includes a pair of drivers attached to the irradiation system at the opposite ends of the movable floor, and a controller that controls these drivers on the basis of the rotation angle of the gantry. Upon the generation of the opening between the irradiation system and one end of the movable floor as the movable floor moves along the semi-cylindrical orbit with the rotation of the gantry, the controller controls the driver in accordance with the rotation angle of the gantry, causing the driver to attract the end of the movable floor toward the irradiation system (see JP-2011-156263-A, paragraph [0056] and FIG. 6). This prevents the space from being formed between the movable floor and the irradiation system in the horizontal floor portion, enabling the medical technician to approach the patient 70 on the bed 63 safely.

However, the conventional treatment cage requires the drivers, the controller, and the driving source for driving those, which has increased the number of components and complicated the system. Complication of the system leads to the higher manufacturing cost. Moreover, the complicated system will easily result in troubles and therefore require the careful maintenance. As thus described, the treatment cage according to the conventional technique needs to be improved from the economical and maintenance point of view.

This embodiment employs the connector 68 including the slide members 69A and 69B and the pair of guide rails 71. With this connector 68, the opposite ends of the movable floor 36 are connected to the pair of side surfaces of the irradiation system 57 opposite to each other in the rotating direction of the gantry 28. This connection enables the treatment cage 35 in this embodiment to omit the drivers, the controller, and the driving sources for those, which have been required in the conventional radiation treatment cage (hereinafter referred to as the conventional treatment cage), and therefore to be simpler than the conventional treatment cage. The simplified treatment cage 35 according to this embodiment experiences fewer troubles and requires less maintenance work.

In this embodiment, with the rotation of the gantry 28, the slide members 69A and 69B attached to the opposite ends of the movable floor 36 slide along the pair of guide rails 71 provided for the pair of side surfaces of the irradiation system 57 opposite to each other in the rotating direction of the gantry 28, and move in the radial direction of the gantry 28. This enables the medical technician 93 to approach the patient 70 on the bed 63 safely without depending on the rotation angle of the gantry 28. That is to say, in this embodiment, it is not necessary to control the drivers to attract the end of the movable floor toward the irradiation system or set it away from the irradiation system, which is different from the conventional treatment cage. Thus, in this embodiment, the time required for one treatment can be shortened and the workability can be improved.

In the conventional treatment cage, the driver is provided for each of the front surface and the rear surface of the irradiation system, and the space where the drivers are installed has restricted the work space. In this embodiment, the connector 68 with the simple structure including the slide members 69A and 69B and the pair of guide rails 71 is provided for the side surface of the irradiation system 57. This configuration can provide the enough work space as compared to the conventional treatment cage. As a result, the workability can be improved in this embodiment.

In the conventional treatment cage, the operation sound caused by the driving possibly makes the patient feel anxiety. In this embodiment, however, the slide members 69A and 69B move along the pair of guide rails 71 synchronizing with the rotation of the gantry 28; thus, such driving sound is not generated. Thus, the patient does not feel anxiety.

In addition, when the irradiation system is present particularly at the position where the rotation angle of the gantry 28 is 150° in the conventional treatment cage (see JP-2011-156263-A, FIG. 6), the opening is generated between the irradiation system and the end of the movable floor near the bed 63. In this point, the drivers are controlled to pull the end of the movable floor, thereby closing the opening in the horizontal floor portion. Normally, before the opening is closed, the interlocking function is activated to prohibit the entry of the medical technician into the treatment cage and the safety of the medical technician is thus secured. However, for some reasons, the medical technician possibly enters the treatment cage and stands on the horizontal floor portion of the movable floor, and the higher safety countermeasure has been demanded. Moreover, the patient on the bed might see out of the treatment cage through the opening until the opening is closed. In this case, the patient may fear of the medical treatment on such a high place.

In this embodiment, the connector 68 connects the side surfaces of the irradiation system 57 and the opposite ends of the movable floor 36. This configuration will not allow the opening to be generated between the irradiation system 57 and the end of the movable floor 36 near the bed 63 when, for example, the irradiation system 57 is at the position where the rotation angle of the gantry 28 is 150° (see FIG. 10). This can further enhance the safety.

In this embodiment, the X-ray transmission plates 39 and 40 can have smaller width in the circumferential direction of the gantry 28. If the opposite ends of the movable floor are attached to the pair of opposite side surfaces of the irradiation system by the drivers as illustrated in FIG. 6 of JP-2011-156263-A, it is necessary to attract or send out the ends of the movable floor with the drivers so as to close the opening generated between the side surface of the irradiation system and the end of the movable floor in the horizontal floor portion. Thus, the amount of movement of the movable floor in the circumferential direction in order to close the opening is increased. In this embodiment, as described above, the opposite ends of the movable floor 36 are attached to the side surfaces of the irradiation system 57 by the slide members 69A and 69B and the pair of guide rails 71. This configuration eliminates the necessity of moving the movable floor in the circumferential direction by the driver and enables the X-ray transmission plates 39 and 40 to have smaller width in the circumferential direction of the gantry 28.

Figure 14:
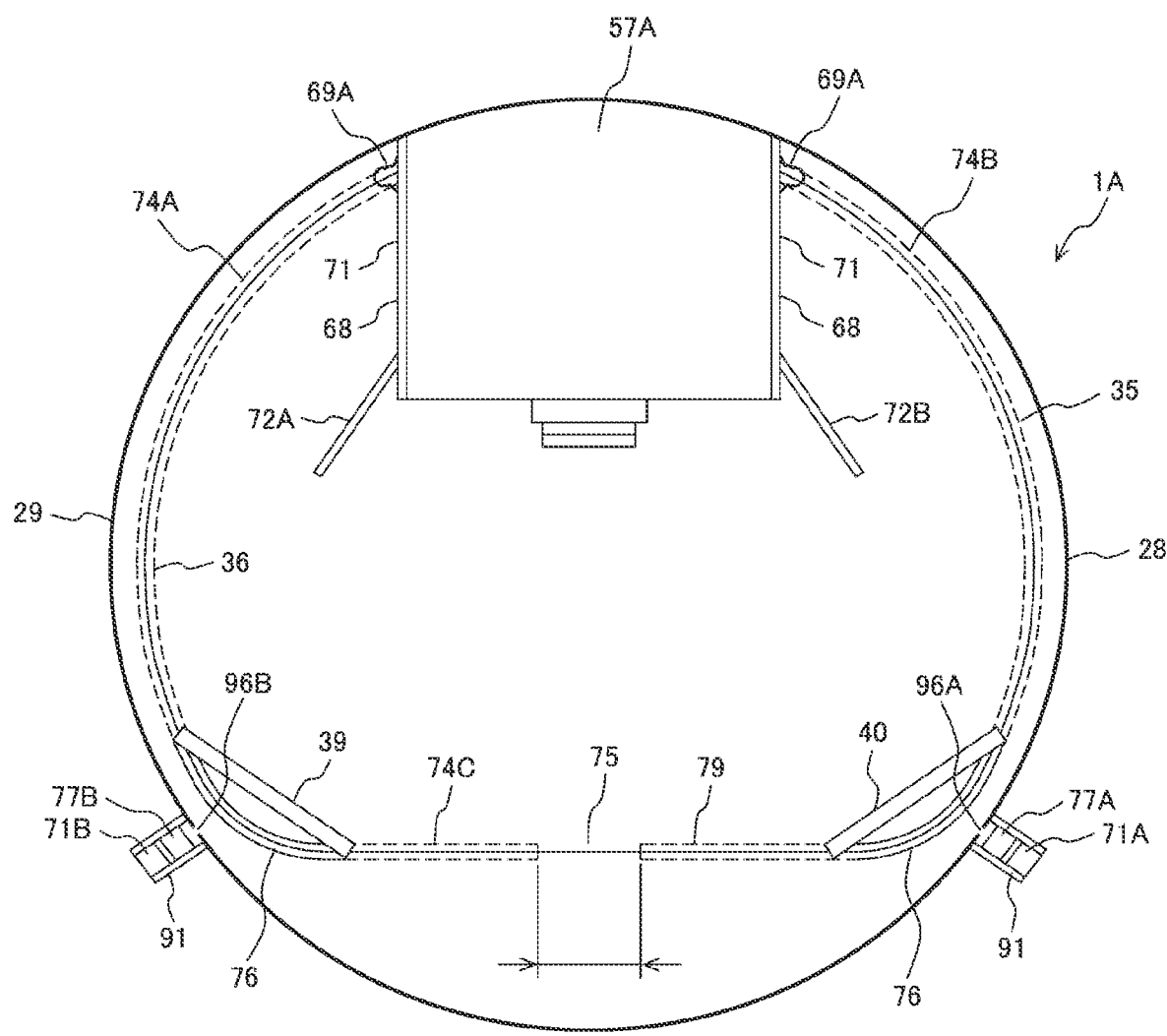
FIG. 14 is a diagram for describing the state of the movable floor of the radiation treatment cage when the rotation angle of the gantry is 0° in a particle therapy system according to a second embodiment corresponding to another preferred embodiment of the present invention.
Figure 15:
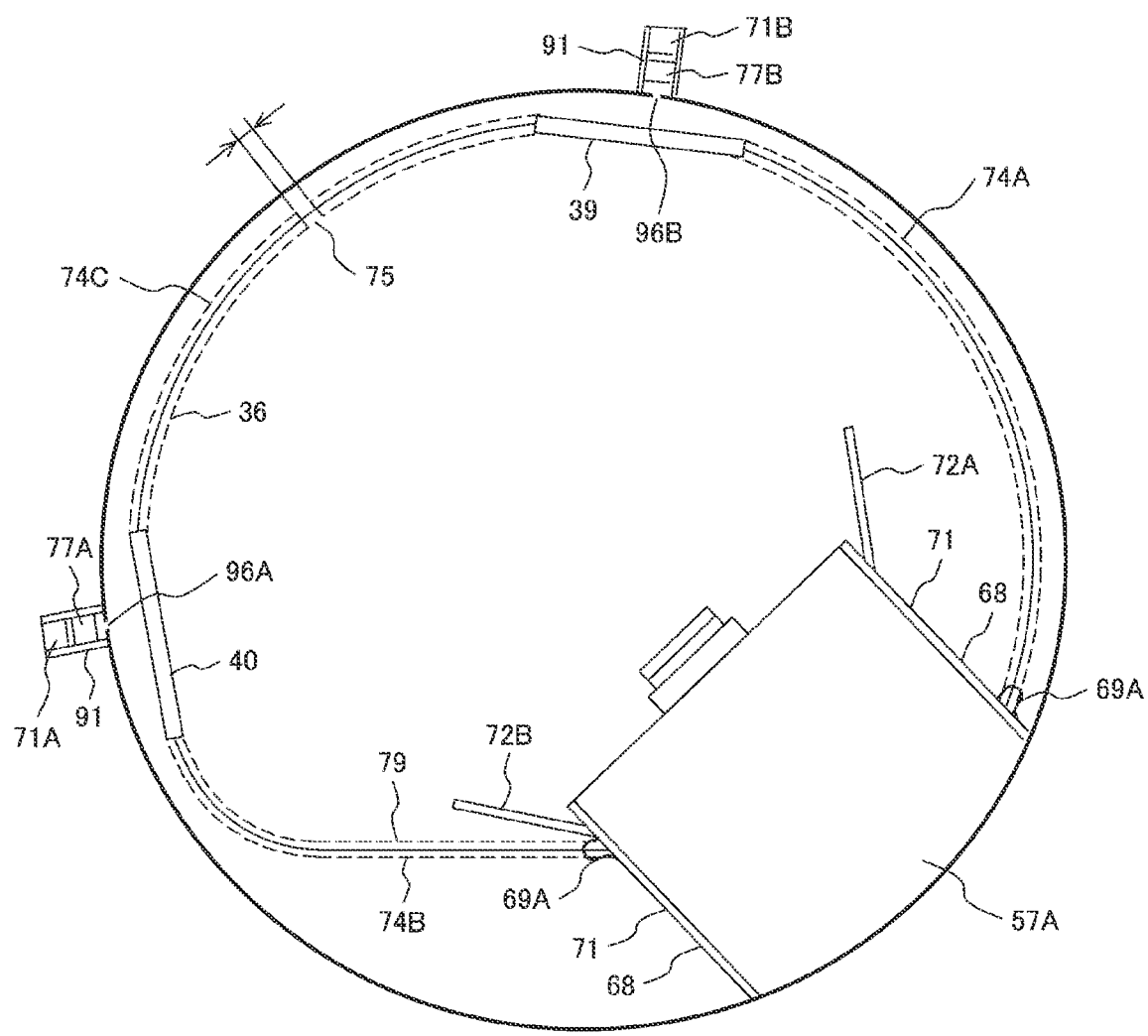
FIG. 15 is a diagram for describing the state of the movable floor of the radiation treatment cage when the rotation angle of the gantry is 135° in the particle therapy system according to the second embodiment.

In this embodiment, the pair of side surfaces of the irradiation system 57 opposite to each other in the rotating direction of the gantry 28 is inclined toward the end of the irradiation system 57 so that the irradiation system 57 has the tapered structure. Description is made of the effect from the irradiation system 57 with such a tapered structure with a comparison to a treatment cage according to a second embodiment to be described below (FIG. 14 and FIG. 15).

In the second embodiment as described below, a pair of side surface of an irradiation system 57A attached to the gantry 28 opposite to each other in the rotating direction of the gantry 28 is parallel to the normal line of the rotation surface of the gantry 28. That is to say, this irradiation system 57A (illustrated with a dashed line in FIG. 10) has a box-like shape.

When the irradiation system 57A is at the position where the rotation angle of the gantry 28 is 135°, the length of the opening 75 is the shortest (see FIG. 15) and the length of each of the first movable floor portion and the second movable floor portion is set so that the first movable floor portion and the second movable floor portion do not interfere with each other at the shortest inner wall length, i.e., so that the length of the opening 75 is 0 or more.

Figure 10:
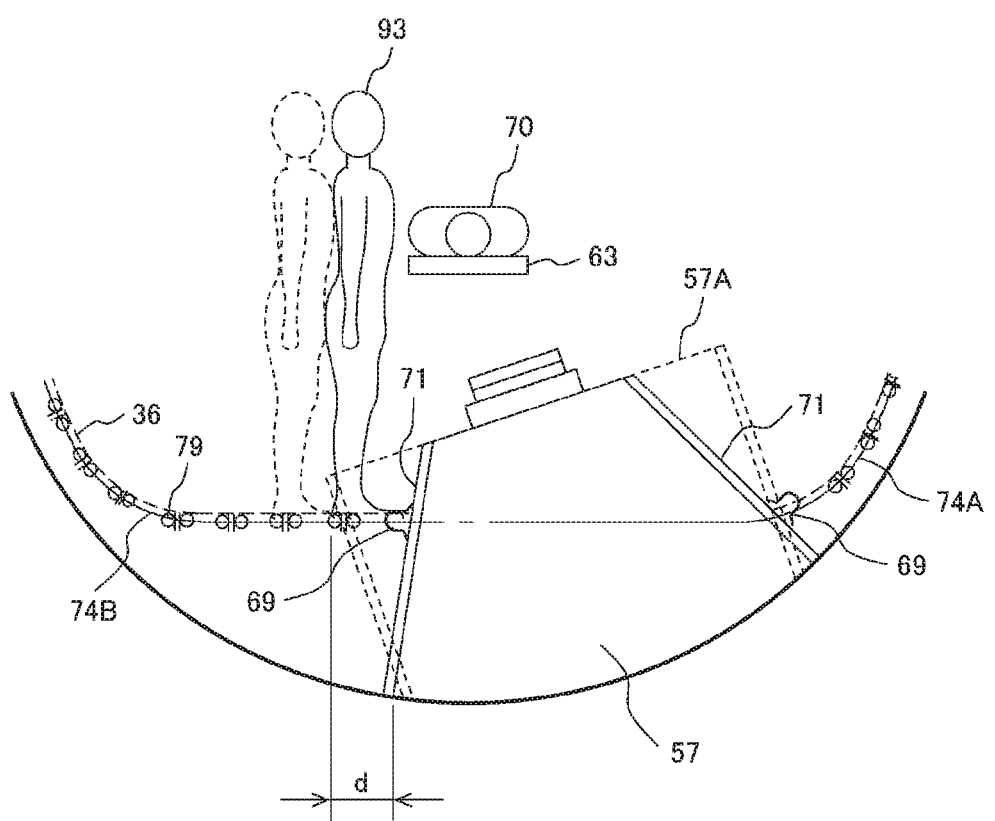
FIG. 10 is a diagram illustrating how easily the medical practitioner on the horizontal floor portion of the movable floor can access the patient on the treatment stand in the particle therapy system according to the first embodiment.

FIG. 10 illustrates the comparison between this embodiment and the second embodiment. Since the irradiation system 57 in this embodiment is different in shape from the irradiation system 57A in the second embodiment, the total length of the first movable floor portion and the second movable floor portion in this embodiment is longer by the length d than the total length of the first movable floor portion and the second movable floor portion in the second embodiment. This is because the width between the slide member 69A attached to the end of the first movable floor portion and attached to one side surface of the irradiation system 57 in the rotating direction of the gantry 28 through the guide rail 71 and the slide member 69A attached to the end of the second movable floor portion and attached to the other side surface of the irradiation system 57 in the rotating direction of the gantry 28 through the guide rail 71 is larger than the width of the irradiation system 57A.

Meanwhile, when the irradiation system 57A is at the position where the rotation angle of the gantry 28 is 0°, the opening 75 generated right below the bed 63 is larger in the second embodiment (see FIG. 14) than the opening 75 in the first embodiment (see FIG. 7). The opening 75 in the second embodiment is larger than the opening 75 in the first embodiment because of the difference d between the total length of the first movable floor portion and the second movable floor portion in this embodiment and the total length of the first movable floor portion and the second movable floor portion in the second embodiment. In other words, this is because of the difference in shape between the irradiation system 57 and the irradiation system 57A. While the irradiation system 57A is at the position where the rotation angle of the gantry 28 ranges from 0° to 60°, the relatively large opening 75 is formed in the horizontal floor portion 79 and this may lead to the safety problem as illustrated in FIG. 14.

In this embodiment, the irradiation system 57 has the tapered structure where the pair of side surfaces of the irradiation system 57 opposite to each other in the rotating direction of the gantry 28 is inclined toward the end of the irradiation system 57. This configuration causes the slide members 69A and 69B attached to the ends of the movable floor 36 to move in the radial direction of the gantry 28 on the inclined side surface of the irradiation system 57. As a result, the change in length in the range corresponding to the irradiation system 57 included in the entire length of the semi-cylindrical orbit 76 in the radial direction of the gantry 28 is suppressed. Thus, the length of the opening 75 generated in the horizontal floor portion 79 is maintained to be very small, which enhances the safety further.

The irradiation system 57A employed in the second embodiment has the box-like shape, and particularly, when the irradiation system 57A is at the position where the rotation angle of the gantry 28 is 150°, the irradiation system 57A interrupts the medical technician 93 approaching the patient 70 on the bed 63 in the treatment room 43, which leads to a problem in workability.

The irradiation system 57 used in this embodiment has the tapered shape, and in particular, when the irradiation system 57 is at the position where the rotation angle of the gantry 28 is 150°, the medical technician 93 can approach the patient 70 more by the length d (see FIG. 10) as compared to the embodiment, and thus the workability can be improved.

In this embodiment, the treatment cage 35 includes the cover 41 and the cover winding system 42; thus, the following effects can be obtained. As described above, while the irradiation system 57 is at the position where the rotation angle of the gantry 28 ranges from 0° to 60°, the microscopic opening 75 is generated in the horizontal floor portion 79 as illustrated in FIG. 7. The length of the opening 75 is maintained to be very small and the safety problem does not occur. For the additional safety, the cover winding system 42 may operate to close the opening 75 with the cover 41. While the irradiation system 57 is at the position where the rotation angle of the gantry 28 ranges from 60° to 180°, the opening 75 is not generated in the horizontal floor portion 79 (see FIG. 8 and FIG. 9); thus the opening 75 does not lead to the safety problem. For the additional safety, the opening 75 may be closed with the cover 41. This can eliminate the anxiety from the operator and the patient.

In the current X-ray computed tomography for positioning the target volume before the target volume is irradiated with the ion beam, in this embodiment, the X-rays emitted from the X-ray sources 71A and 71B are delivered to the target volume of the patient 70 while the gantry 28 is rotated. In this current X-ray CT, however, the X-ray emitted from one X-ray source, for example the X-ray source 71A, may be delivered to the target volume while the gantry 28 is rotated. That is to say, the X-ray emitted from the X-ray source 71A passes through the collimator 77A and the penetration hole 96A and further through the X-ray transmission portion 95 of the X-ray transmission plate 40 before being delivered to the target volume. The X-ray having transmitted through the target volume is detected by each X-ray detector included in the X-ray detection system 72A. In this case, the gantry 28 is rotated in the range of, for example, 365°. Based on the X-ray detection signals output from the X-ray detectors of the X-ray detection system 72A, the X-ray intensity information can be obtained. The image information formation system forms the tomographic information including the target volume of the patient 70 on the basis of the X-ray intensity information for each X-ray detector of the X-ray detection system 72A and each measured rotation angle of the gantry 28. The positioning data generation system forms the aforementioned bed positioning data on the basis of the current tomographic information and the reference tomographic information.

In the first embodiment, the X-ray sources 71A and 71B are circulated around the patient 70 on the bed 63 by rotating the gantry 28 while the X-rays are emitted from the X-ray sources 71A and 71B. Thus, the current tomographic information is obtained. In contrast, in JP-H-1-209077-A, the target volume is positioned without circulating the X-ray source emitting the X-ray around the patient 70 on the bed 63. In such positioning of the target volume, the particle therapy system 1 according to this embodiment can be employed. For example, the gantry 28 is rotated up to a rotation angle of 45° so that the X-ray 78A from the X-ray source 71A travels in the Z-direction and the X-ray 78B from the X-ray source 71B travels in the X-direction.

As described above, the bed controller controls the driving mechanisms for the treatment stand 62 to move the patient 70 on the bed 63 to the predetermined position. In the state that the rotation angle of the gantry 28 is 45°, the X-ray 78A emitted upward from the X-ray source 71A travels through the penetration hole 96A and further through the X-ray transmission portion 95 of the X-ray transmission plate 40 before the X-ray 78A is delivered to the target volume of the patient 70 on the bed 63 from below. The X-ray 78A having transmitted through the target volume is detected by each X-ray detector included in the X-ray detection system 72A.

The X-ray 78B emitted horizontally from the X-ray source 71B travels through the penetration hole 96B and further through the X-ray transmission portion 95 of the X-ray transmission plate 39 before the X-ray 78B is delivered horizontally to the target volume of the patient 70 on the bed 63. The X-ray 78B having transmitted through the target volume is detected by each X-ray detector included in the X-ray detection system 72B.

With the X-ray detection signals output from the X-ray detectors included in the X-ray detection system 72A and the X-ray detection signals output from the X-ray detectors included in the X-ray detection system 72B, the positioning data generation system provides the amount of movement of the bed 63 in the X-Y plane, the rotation angle of the bed 63, and the amount of movement of the bed 63 in the X-Z plane as described in JP-H-1-209077-A. The amounts of movement of the bed 63 and the rotation angle of the bed 63 are input to the bed controller, and the bed controller controls the corresponding driving mechanism for the treatment stand 62, thereby positioning the bed 63 before the target volume is irradiated with the ion beam.

The treatment cage 35 used in the first embodiment includes the cover 41 and the cover winding system 42. The operation of the cover winding system 42 closes the opening 75 in the horizontal floor portion 79 with the cover 41, and eliminates the anxiety from the patient 70 and the medical technician 93 in the treatment room 43. For this reason, it is preferable to have the cover 41 and the cover winding system 42. However, since the opening 75 does not lead to the safety problem as below, the treatment cage 35 does not necessarily include the cover 41 and the cover winding system 42. For example, while the irradiation system 57 is present at the position where the rotation angle of the gantry 28 ranges from 0° to 60°, the opening 75 is generated in the horizontal floor portion 79 (see FIG. 7). As described above, with the tapered structure of the irradiation system 57, the length of the opening 75 can be maintained to be very small, so that the opening 75 does not lead to the safety problem. Moreover, while the irradiation system 57 is present at the position where the rotation angle of the gantry 28 ranges from 60° to 180°, the opening 75 is not generated in the horizontal floor portion 79 (see FIG. 9), so that the opening 75 does not lead to the safety problem.

By omitting the cover 41 and the cover winding system 42, the number of components of the treatment cage can be reduced and the treatment cage can be simplified further as compared to the first embodiment.

In the first embodiment, each of the pair of side surfaces of the irradiation system 57 opposite to each other in the rotating direction of the gantry 28 is provided with the guide rail 71; however, the guide rail 71 may alternatively be provided for each of the front surface and the rear surface of the irradiation system 57. That is to say, if the guide rail 71 is provided for each of the front surface and the rear surface of the irradiation system 57 in parallel to the side surface of the irradiation system 57 facing in the rotating direction of the gantry 28, the slide members 69A and 69B attached to the end of the movable floor 36 can be separately moved along the guide rails 71 provided for the front surface and the rear surface of the irradiation system 57, which is similar to the first embodiment. For example, when the irradiation system 57 is present at the position where the rotation angle of the gantry 28 is 150°, the connector 68 connects between the irradiation system 57 and the end of the movable floor 36. In this case, the opening 75 is not generated between the end of the movable floor 36 and the irradiation system 57 in the horizontal floor portion 79. This can increase the safety like in the first embodiment (see FIG. 10). Note that the front surface of the irradiation system 57 corresponds to the side surface of the irradiation system 57 on the treatment stand 62 side, and the rear surface of the irradiation system 57 corresponds to the side surface of the irradiation system 57 on the back panel 46 side.

This embodiment employs two sets of X-ray sources and X-ray detection systems: the X-ray source 71A and the X-ray detection system 72A; and the X-ray source 71B and the X-ray detection system 72B. However, one of these sets may be employed. If one set of X-ray source and X-ray detection system is used, the movable floor 36 includes one X-ray transmission plate opposite to each of one set of X-ray source and X-ray detection system. In the case of using one set of X-ray source and X-ray detection system, the position of the target volume when the ion beam is delivered cannot be known; however, since the X-ray can be delivered to the patient from the X-ray source while the gantry 28 is rotated, the positioning of the target volume is possible.

The first embodiment is similarly applicable to a particle therapy system including a gantry rotating in the range of 180° (a half gantry) instead of the gantry 28 rotating in the range of 360°.

Second Embodiment

A particle therapy system according to the second embodiment corresponding to another preferred embodiment of the present invention is described with reference to FIG. 14 and FIG. 15.

A particle therapy system 1A according to this embodiment includes the irradiation system 57A instead of the irradiation system 57 in the particle therapy system 1 according to the first embodiment. The irradiation system 57A employed in the particle therapy system 1A has the box-like shape, which is different from the irradiation system 57. A pair of side surfaces of the irradiation system 57A opposite to each other in the rotating direction of the gantry 28 is parallel to the normal line of the rotation surface of the gantry 28 (the side surfaces of the irradiation system 57A are not inclined). The other structure of the particle therapy system 1A is the same as the particle therapy system 1 according to the first embodiment.

The irradiation system 57A has the box-like shape and is not tapered; thus, the particle therapy system 1A according to this embodiment does not provide the effect of the particle therapy system 1 according to the first embodiment: the change in the length corresponding to the irradiation system 57 included in the entire length of the semi-cylindrical orbit 76 in the radial direction of the gantry 28 is suppressed. In the particle therapy system 1A, however, the connector 68 connects between the opposite ends of the movable floor 36 and the pair of side surfaces of the irradiation system 57A opposite to each other in the rotating direction of the gantry 28, so that the effect from the connector 68 can be obtained. In this embodiment, the effects obtained from the first embodiment other than the effect that the change in the length corresponding to the irradiation system 57 included in the entire length of the semi-cylindrical orbit 76 in the radial direction of the gantry 28 is suppressed can be achieved.

In this embodiment, however, the opening 75 (see FIG. 14) generated in the horizontal floor portion 79 while the irradiation system 57A is present at the position where the rotation angle of the gantry 28 is 0° is larger than the opening 75 (see FIG. 7) generated in the horizontal floor portion 79 while the irradiation system 57 is present at the position where the rotation angle of the gantry 28 is 0° in the first embodiment; thus, the second embodiment is inferior to the first embodiment in point of safety. In order to improve the safety by solving this problem, the structure of the treatment cage 35 used in the second embodiment may be changed a little as described below.

In the second embodiment, for example, the movable floor 36 including the two cover winding systems 42 may be used. In this case, the movable floor 36 includes, for example, three movable floor portions: the first movable floor portion (footboard group 74A), the second movable floor portion (footboard group 74B), and a third movable floor portion (X-ray transmission plate 39, footboard group 74C, and X-ray transmission plate 40), and further includes the cover winding system (first cover winding system) 42 disposed between the first movable floor portion and the third movable floor portion and the cover winding system (second cover winding system) 42 disposed between the second movable floor portion and the third movable floor portion. In this case, the movable floor 36 has a latch structure (not illustrated) that fixes the intermediate third movable floor portion to the gantry 28 in the rotating circumferential direction. The other structure is the same as the particle therapy system 1 in the first embodiment.

The movable floor 36 includes the first movable floor portion, the second movable floor portion, and the third movable floor portion. This configuration does not allow the generation of the opening 75 in the horizontal floor portion 79 while the irradiation system 57A is present at the position where the rotation angle of the gantry 28 is 0°, which is similar to the first embodiment. Thus, the opening 75 of the movable floor 36 does not lead to the safety problem. If the opening 75 generated between the first movable floor portion and the third movable floor portion (between the footboard 38 at the end of the first movable floor portion and the X-ray transmission plate 39 adjacent to this footboard 38) or the opening 75 generated between the second movable floor portion and the third movable floor portion (between the footboard 38 at the end of the second movable floor portion and the X-ray transmission plate 40 adjacent to this footboard 38) exists in the horizontal floor portion 79, the first cover winding system 42 or the second cover winding system 42 is operated to close the opening 75 in the horizontal floor portion 79 with the cover 41. This eliminates the anxiety from the medical technician 93 and the patient 70. In the case of putting the cover 41 on the opening 75 in the horizontal floor portion 79 by the operation of the first and second cover winding systems 42, the cover 41 is preferably pulled out from the X-ray transmission plate 39 or 40 side toward the footboard 38 of the first movable floor portion or the second movable floor portion so that the pulled cover 41 is not overlapped on the X-ray transmission plate 39 or 40.

Third Embodiment

Description is hereinafter made of a particle therapy system according to a third embodiment corresponding to another preferred embodiment of the present invention with reference to FIG. 16.

The particle therapy system 1 according to the first example employs the ion beam generator 2 including the synchrotron accelerator 3 but a particle therapy system 1B according to this embodiment employs an ion beam generator 2A including a cyclotron accelerator 83.

Figure 16:
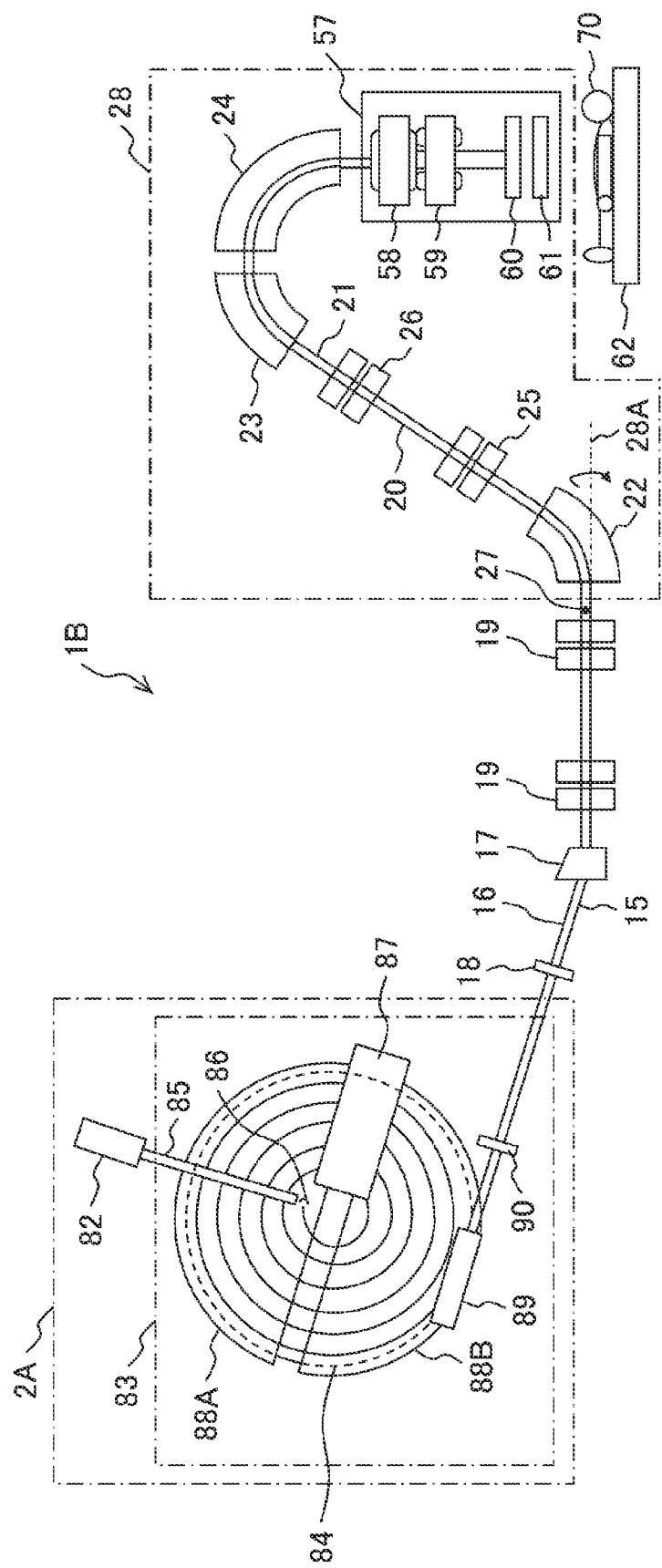
FIG. 16 is a structure diagram illustrating a particle therapy system according to a third embodiment corresponding to another preferred embodiment of the present invention.

The particle therapy system 1B includes, as illustrated in FIG. 16, the ion beam generator 2A, the HEBT 15, the GABT 20, the gantry 28, and the irradiation system 57. The structure of the particle therapy system 1B is the same as that of the particle therapy system 1 except the ion beam generator 2A. Here, the ion beam generator 2A, in which the particle therapy system 1B is different from the particle therapy system 1, is mainly described.

The ion beam generator 2A includes an ion source 82 and the cyclotron accelerator 83. The cyclotron accelerator 83 includes a circular vacuum vessel 84, bending magnets 88A and 88B, a radiofrequency accelerator 87, and an extraction septum magnet 89. A vacuum duct 85 has one end connected to the ion source 82 and the other end extending to the center of the vacuum vessel 84 and connecting to the vacuum vessel 84. An injection electrode 86 curving on the horizontal plane is disposed in the vacuum vessel 84 near the open end of the vacuum duct 85. The bending magnets 88A and 88B have the semi-circular shape and are disposed with their linear portions facing each other, and cover the upper and lower surfaces of the vacuum vessel 84.

The septum magnet 89 provided for the ion beam exit of the vacuum vessel 84 is connected to the beam path 16 of the HEBT 15. A degrader 90 with a plurality of metal plates is attached to the beam path 16 between the septum magnet 89 and a quadrupole magnet 18. The degrader 90 has a function of adjusting the energy of the ion beam emitted from the cyclotron accelerator 83, and includes a plurality of metal plates with different thickness (not illustrated). These metal plates are movable in a direction perpendicular to the beam path 16. One or more of such metal plates with different thicknesses is inserted into the beam path 16 across the beam path 16, thereby controlling the attenuation amount of energy of the ion beam traveling through the beam path 16. As a result, the energy of the ion beam to be delivered to the target volume of the patient 70 can be changed and the ion beam can be delivered to each layer existing in the target volume in the depth direction.

In this embodiment, the movable floor 36 includes the X-ray transmission plates 39 and 40, the X-ray sources 71A and 71B and the collimators 77A and 77B are attached to the outer surface of the rotary drum 29, and the X-ray detection systems 72A and 72B are attached to the irradiation system 57 and this is similar to the first embodiment.

The particle therapy system 1B according to this embodiment can provide the effect obtained in the first embodiment.

In the second and third embodiments, the positioning of the target volume can be carried out before the irradiation with the ion beam as described in the first embodiment, and additionally, the position of the target volume and the effect from the irradiation with the ion beam can be known during the irradiation of the target volume with the ion beam.

What is claimed is:
1. A particle therapy system comprising:
a gantry;
an irradiation system which is attached to the gantry and irradiates an ion beam;
a surrounding member installed in the gantry, having an orbit including an arc-like portion and a horizontal portion communicating with the arc-like portion, and configured to move along the orbit;

an X-ray detection system disposed inside the surrounding member, attached to the irradiation system, and detecting an X-ray from an X-ray source; and the X-ray source disposed outside the surrounding member and disposed opposite to the X-ray detection system, wherein the surrounding member includes a plurality of areas in a circumferential direction including an X-ray transmission area made of X-ray transparent material and other areas made of another material which is different from the X-ray transparent material, the X-ray transmission area being arranged between the other areas in the circumferential direction, wherein the X-ray transmission area is disposed between the X-ray source and the X-ray detection system, wherein the surrounding member includes a plurality of connected footboard members, and a width $W_3$ of the X-ray transmission area in a circumferential direction of the gantry is larger than a width $W_1$ of the footboard member in the circumferential direction, and wherein a path of the X-ray through the X-ray transmission area varies based on a rotational position of the surrounding member along the orbit.

2. The particle therapy system according to claim 1, wherein the plurality of connected footboard members are made of the another material which is different from the X-ray transparent material.

3. The particle therapy system according to claim 2, wherein the X-ray transmission area is disposed between the adjacent footboard members and connected to the footboard members.

4. The particle therapy system according to claim 1, wherein the X-ray transmission area is an X-ray transmission member having a width $W_2$ of the X-ray transmission member in a circumferential direction of the gantry is larger than the width $W_1$.

5. The particle therapy system according to claim 1, wherein the X-ray source is attached to the gantry.

6. The particle therapy system according to claim 2, wherein the X-ray transmission area is an X-ray transmission member having a width $W_2$ of the X-ray transmission member in a circumferential direction of the gantry is larger than a width $W_1$ of the footboard member in the circumferential direction and is less than or equal to a value obtained by subtracting the width $W_1$ from a width $W_H$ of a horizontal floor portion of the surrounding member that is located in the horizontal portion of the orbit.

7. The particle therapy system according to claim 2, wherein the X-ray transmission area is an X-ray transmission member that includes a plate-shaped metal member, and wherein a width $W_3$ of the X-ray transmission area in the circumferential direction is smaller than the width $W_2$ of the X-ray transmission member.

8. The particle therapy system according to claim 5, wherein:
the X-ray source is disposed outside the gantry and attached to an outer surface of the gantry; and
an X-ray transmission hole is formed at a position on the gantry opposite to the X-ray source.

9. The particle therapy system according to claim 5, wherein
the X-ray source includes a first X-ray source and a second X-ray source;

the first X-ray source and the second X-ray source are disposed apart from each other in a circumferential direction of the gantry;
the X-ray detection system includes a first X-ray detection system and a second X-ray detection system;
the first X-ray detection system is disposed opposite to the first X-ray source; and
the second X-ray detection system is disposed opposite to the second X-ray source.

10. The particle therapy system according to claim 9, wherein
the X-ray transmission area is an X-ray transmission member that includes a first X-ray transmission member and a second X-ray transmission member;
wherein the first X-ray transmission member is disposed opposite to the first X-ray source; and
wherein the second X-ray transmission member is disposed opposite to the second X-ray source.

11. The particle therapy system according to claim 10, wherein a width $W_2$ of each of the first and second X-ray transmission members in a circumferential direction of the gantry is larger than a width $W_1$ of the footboard member in the circumferential direction and is less than or equal to a value obtained by subtracting the width $W_1$ from a width $W_H$ of the horizontal floor portion of the surrounding member that is located in the horizontal portion of the orbit.

12. The particle therapy system according to claim 11, wherein the width $W_3$ of the X-ray transmission area in the circumferential direction is smaller than the width $W_2$ of the X-ray transmission member.

13. The particle therapy system according to claim 1, further comprising a pair of connectors provided for the irradiation system,
the connectors connecting between each of opposite ends of the surrounding member and each of a pair of opposite side surfaces of the irradiation system in a manner that movement in a radial direction of the gantry is possible.

14. The particle therapy system according to claim 13, wherein the connector comprises a guide member attached to the side surface of the irradiation system and extending in the radial direction of the gantry, and a slide member attached to the end of the movable floor member and attached movably to the guide member.

15. The particle therapy system according to claim 13, wherein the pair of side surfaces of the irradiation system opposite to each other in the rotating direction of the gantry is tapered toward a center axis of the gantry.

16. The particle therapy system according to claim 10, wherein the surrounding member includes a first movable floor portion including a plurality of the footboard members connected bendably and the second X-ray transmission member, and a second movable floor portion including another plurality of the footboard members connected bendably and the first X-ray transmission member.

17. The particle therapy system according to claim 13, further comprising a cover that closes an opening generated in the surrounding member, and a cover winding system that moves the cover.

18. The particle therapy system according to claim 1, further comprising an accelerator that accelerates the ion beam, and a beam transport that is connected to the accelerator and guides the ion beam from the accelerator to the irradiation system.

* * * * *